(12) United States Patent
Rownaghi et al.

(10) Patent No.: US 11,192,094 B2
(45) Date of Patent: Dec. 7, 2021

(54) ZEOLITE MONOLITH COMPOSITIONS AND METHODS FOR THE CATALYTIC CRACKING OF ALKANES

(71) Applicant: The Curators of the University of Missouri, Columbia, MO (US)

(72) Inventors: Ali A. Rownaghi, Rolla, MO (US); Xin Li, Rolla, MO (US); Fateme Rezaei, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/585,968

(22) Filed: Sep. 27, 2019

(65) Prior Publication Data

US 2020/0101447 A1 Apr. 2, 2020

Related U.S. Application Data

(60) Provisional application No. 62/738,185, filed on Sep. 28, 2018.

(51) Int. Cl.
| | | |
|---|---|---|
| *B01J 29/85* | (2006.01) | |
| *C07C 4/06* | (2006.01) | |
| *B01J 29/00* | (2006.01) | |
| *B01J 29/40* | (2006.01) | |
| *B01J 29/08* | (2006.01) | |
| *B01J 29/48* | (2006.01) | |
| *B01J 29/46* | (2006.01) | |
| *B01J 35/04* | (2006.01) | |
| *B01J 35/10* | (2006.01) | |

(Continued)

(52) U.S. Cl.
CPC ........... *B01J 29/005* (2013.01); *B01J 29/084* (2013.01); *B01J 29/146* (2013.01); *B01J 29/40* (2013.01); *B01J 29/46* (2013.01); *B01J 29/48* (2013.01); *B01J 29/85* (2013.01); *B01J 35/04* (2013.01); *B01J 35/1038* (2013.01); *B01J 35/1042* (2013.01); *B01J 35/1061* (2013.01); *B01J 35/1066* (2013.01); *B33Y 10/00* (2014.12); *B33Y 80/00* (2014.12); *C07C 4/06* (2013.01); *C07C 2529/10* (2013.01); *C07C 2529/42* (2013.01)

(58) Field of Classification Search
CPC ...... B01J 29/005; B01J 29/084; B01J 29/146; B01J 29/40; B01J 29/46; B01J 29/48; B01J 29/85; B01J 35/04; B01J 37/00; B33Y 80/00; C07C 4/06; C07C 2529/10; C07C 2529/42
See application file for complete search history.

(56) References Cited

U.S. PATENT DOCUMENTS

2019/0001311 A1* 1/2019 Rownaghi ................ B01J 29/46

OTHER PUBLICATIONS

Xin Li, Wenbin Li, Fateme Rezaei, Ali Rownaghi, Catalytic cracking of n-hexane for producing light olefins on 3D-printed monoliths of MFI and FAU zeolites, Chemical Engineering Journal, vol. 333, 2018, pp. 545-553 (Year: 2017).*

(Continued)

*Primary Examiner* — David M Brunsman
(74) *Attorney, Agent, or Firm* — Hovey Williams LLP

(57) ABSTRACT

Porous zeolite monolith compositions for the catalytic cracking of alkanes. The compositions may be prepared layer by layer using a 3D printer such that the compositions comprise a plurality of micropores and a plurality of mesopores and may be characterized by macro-meso-microporosity.

18 Claims, 21 Drawing Sheets

(51) Int. Cl.
*B33Y 10/00* (2015.01)
*B33Y 80/00* (2015.01)
*B01J 29/14* (2006.01)

(56) References Cited

OTHER PUBLICATIONS

Z.Y. Zakaria, J. Linnekoski, N.A.S. Amin, "Catalyst screening for conversion of glycerol to light olefins", Chemical Engineering Journal, vols. 207-208, (2012) pp. 803-813 (Year: 2012).*

Zhang et al., "Synthesis of core-shell ZSM-5@meso-SAPO-34 composite and its application in methanol to aromatics", RSC Adv., 2015, 5, 55825 (Year: 2015).*

Xin Li, Wenbin Li, Fateme Rezaei, Ali Rownaghi, Catalytic cracking of n-hexane for producing light olefins on 3D-printed monoliths of MFI and FAU zeolites, Chemical Engineering Journal, vol. 333, 2018, pp. 545-553 (available online Oct. 1, 2017) (Year: 2017).*

* cited by examiner

ZEOLITE MONOLITH COMPOSITIONS AND METHODS FOR THE CATALYTIC CRACKING OF ALKANES

CROSS-REFERENCE TO RELATED APPLICATIONS

This application claims the benefit of U.S. Provisional Application Ser. No. 62/738,185, entitled "3D Printed Monoliths of MFI and FAU Zeolites and their Applications in Catalytic Cracking of n-Hexane," filed Sep. 28, 2018, the contents of which are incorporated by reference herein, for all purposes, in its entirety.

FIELD

The present disclosure is broadly concerned with compositions and methods for the catalytic cracking of alkanes. The disclosure is also concerned with porous 3D-printed zeolite monolith compositions for the catalytic cracking of alkanes, as well as methods of preparing such compositions and methods of the use of such compositions for the catalytic cracking of alkanes.

BACKGROUND

Catalytic cracking of light alkanes such as n-hexane is of great importance because it focuses on the production of light olefins in a more energy-efficient and environmentally friendly way, as compared with traditional thermal cracking. Light olefins generally refer to ethylene, propylene and butylene, which are significant raw materials in downstream chemical industry like polymers and alkylbenzenes production. Acidic zeolites are the most broadly used catalysts for the conversion of n-hexane due to their intrinsic acidity, framework variety and manipulatable pore structure. In particular, catalytic cracking of alkanes over zeolites is an attractive alternative to the traditional thermal cracking for production of benzene, toluene, and xylene (BTX), as well as light olefins.

Among the hundreds of zeolites with various frameworks, HZSM-5, H-Beta and HY zeolites are the most extensively investigated catalysts for this reaction and the generally accepted "carbenium ion" theory has been proposed as the mechanism of the alkanes cracking over acidic zeolite. As microporous crystalline aluminosilicates with uniform and ordered networks, these zeolites are characterized by high surface area, outstanding stability and specific shape selectivity. On the other hand, due to the narrow intracrystalline micropores, these materials suffer from slow diffusion and restricted mass transfer of the reactants and products, which greatly affect their activity, selectivity and lifetime. Accordingly, additional catalysts for the catalytic cracking of alkanes, particularly, light alkanes, is desirable. Additionally, catalysts exhibiting advantageous selectivity to light olefins is also desirable.

ZSM-5 zeolite, with MFI framework, has also been studied in the context of catalytic cracking due to its high catalytic activity and shape selectivity. However, one of the major problems in alkane catalytic cracking process over ZSM-5 is the coke formation which inhibits the reaction either by blocking access of reactant molecules to the acid sites in the micropores or by competitive removal of acid sites. It has been well established that the number and nature of the acid sites clearly influence coke formation. To reduce the rate of coke formation and hence prevent rapid catalyst deactivation, various approaches such as optimization of acidity, change of particle size, alteration of textural properties, and modification with heteroatoms, mainly metals have been tried. However, additional catalyst compositions for the catalytic cracking of alkanes, including additional ZSM-5 compositions, exhibiting reduced coke formation as well as other advantageous catalytic properties are desirable.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 3A is a SEM micrograph of a HZSM-5 monolith, according to an exemplary embodiment of the present disclosure;

FIG. 3B is a SEM micrograph of a HY monolith, according to an exemplary embodiment of the present disclosure;

FIG. 3C is a SEM micrograph of a HZSM-5 monolith with SAPO-34 growth, according to an exemplary embodiment of the present disclosure;

FIG. 3D is a SEM micrograph of a HY monolith with SAPO-34 growth, according to an exemplary embodiment of the present disclosure;

DETAILED DESCRIPTION

Figure 1:
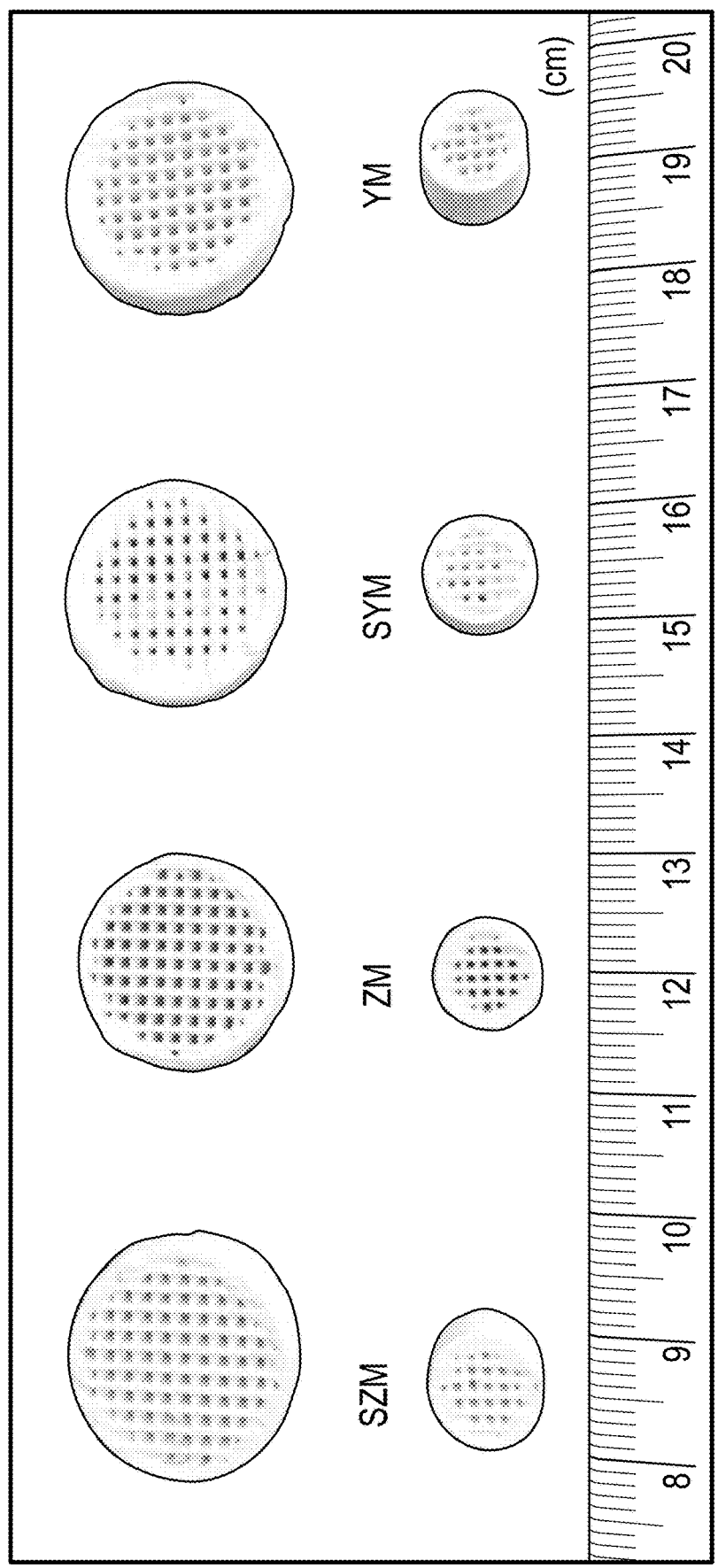
FIG. 1 is an optical image of the 3D-printed monoliths obtained according to Examples 1 and 2, according to an exemplary embodiment of the present disclosure.

The present disclosure provides compositions and methods for the catalytic cracking of alkanes, in particular light alkanes. The presently disclosed compositions have unexpectedly been discovered to exhibit advantageous catalytic activity and selectivity to light olefins. The advantageous characteristics of the presently disclosed compositions are, at least in some instances, the result of the presently disclosed controlled fabrication processes for preparing the catalytic compositions disclosed herein, that may include, for example, controlled 3D-printing as well as controlled acidity, controlled coating processes, scaled down crystal size, altered pore structure, and metal-doping.

In at least some instances, the presently disclosed porous 3D-printed zeolite monolith compositions exhibit advantageous surface area, porosity, acidity, and pore structure for the catalytic cracking of alkanes. In particular, the presently disclosed HZSM-5 zeolite monolith compositions unexpectedly exhibit a greater degree of stable activity in n-hexane cracking and higher selectivity to light olefins than its powder counterpart. In particular, HY zeolite monolithic catalysts exhibit surprisingly high selectivity for light olefins. Additionally, porous 3D-printed zeolite monolith compositions coated with SAPO-34 exhibit advantageous n-hexane cracking catalytic activity and significantly improved catalytic selectivity to BTX (benzene, toluene and xylene) as compared to HY monoliths that are not coated.

The present disclosure also provides metal doped 3D-printed porous zeolite monolith catalyst compositions. For example, Cr, Cu, Ni, and Y-doped 3D-printed ZSM-5 monoliths synthesized by adding metal nitrate precursors directly into the ZSM-5 slurry are provided. Such metal-doped 3D-printed ZSM-5 monolith compositions may be prepared by a process that integrates the modification step with the additive manufacturing of the structured catalysts. The crystal structure and the frameworks of the ZSM-5 zeolites are retained after the metal doping, despite the fact that corresponding metal oxides are formed in the 3D-printed monoliths. It has been found that both the porosity and the acidity of the monoliths are influenced by metal modification. The metal doped 3D-printed porous zeolite monolith catalysts have unexpectedly been found to exhibit advantageous catalytic activity and selectivity. In particular, it has been discovered that Cr, Cu, and Ni modification favors the production of BTX in n-hexane catalytic cracking, whereas the addition of Y in the monoliths promotes selectivity towards light olefins. Moreover, temperature and time-on-streams has been found to be a significant factor affecting the product distribution of the presently disclosed metal doped 3D-printed porous zeolite monolith catalyst compositions. At lower temperatures, the metal doped 3D-printed porous zeolite monolith catalysts exhibit relatively steady catalytic activity during the reaction time and exhibited lower light olefins selectivity, whereas, at higher temperatures, the light olefins selectivity increased with reaction evolution for all compositions and the maximum selectivity of about 50% was observed on YZM.

According to at least one aspect of the present disclosure, a composition for the catalytic cracking of alkanes is provided. The composition may include a porous zeolite monolith. The porous zeolite monolith may in some instances be prepared layer by layer using a 3D printer. In such cases, the porous zeolite monolith is a 3D-printed porous zeolite monolith. The porous zeolite monolith may include interconnected channels. In at least some instances, the interconnected channels may be formed by layer-by-layer deposition using a 3D printer. In some instances, the porous zeolite monolith may have or be characterized by macro-meso-microporosity.

As used herein, the term "porous," refers to a solid material in which pores and/or channels are arranged. A "macroporous material" or a material exhibiting "macroporosity" is a material having pores larger than 50 nm in diameter. A "mesoporous material" or a material exhibiting "mesoporosity" is a material containing pores with diameters between 2 nm and 50 nm. A "microporous material" or a material exhibiting "microporosity" is a material having pores smaller than 2 nm in diameter. As used herein, a material that comprises or is characterized by "macro-meso-microporosity" is a material that exhibits macroporosity (e.g., has some pores that are larger than 50 nm in diameter), mesoporosity (e.g., has some pores with diameters between 2 nm and 50 nm, and microporosity (e.g., has some pores that are smaller than 2 nm in diameter).

According to at least one aspect of the present disclosure, the porous zeolite monolith may include a plurality of micropores and a plurality of mesopores. In some instances, the micropores may have a diameter of greater than 15 nanometers and the mesopores may have a diameter of from 2 nanometers to 15 nanometers. The porous zeolite monolith may be selected from the group consisting of a ZSM-5 zeolite monolith, a HZSM-5 zeolite monolith, and a HY zeolite monolith. In some instances, the porous zeolite monolith may be a 3D-printed ZSM-5 zeolite monolith comprising a MFI framework. In other instances, the porous zeolite monolith may be a 3D-printed HZSM-5 zeolite monolith comprising a MFI framework. In still other instances, the porous zeolite monolith may be a 3D-printed HY zeolite monolith comprising a FAU framework.

In some cases, a silicoaluminophosphate with chabazite (SAPO-34) framework may be coated onto the porous zeolite monolith. In such cases, the porous zeolite monolith further comprises a coating, the coating comprising a silicoaluminophosphate with chabazite (SAPO-34) framework. In some instances, the SAPO-34 framework comprises a coating on the porous zeolite monolith formed by a secondary growth method.

According an aspect of the present disclosure, the porous zeolite monolith may be a metal-doped porous zeolite monolith comprising a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof. For example, the metal-doped porous zeolite monolith may be formed from a zeolite paste doped with a metal precursor. In some instances, the metal precursor may be a metal nitrate compound. For example, the metal precursor may be selected from the group consisting of $Cr(NO_3)_3 \cdot 9H_2O$, $Cu(NO_3)_2 \cdot 2.5H_2O$, $Ni(NO_3)_2 \cdot 6H_2O$, and $Y(NO_3)_3 \cdot 6H_2O$.

In some instances, the metal-doped porous zeolite monolith may comprise from about 1 wt % to about 20 wt % metal content, or from about 2.5 wt % to about 12 wt % metal content, or from about 5 wt % to about 10 wt % metal content, or from about 9 wt % to about 12 wt % metal content, or from about 2.5 wt % to about 15 wt % metal content, or from about 5 wt % to about 15 wt % metal content. In some instances, the the metal-doped porous zeolite monolith is characterized by a metal loading of 1 wt % to about 20 wt %, or by a metal loading of 2.5 wt % to about 12 wt %, or by a metal loading of 5 wt % to about 10 wt %, or by a metal loading of 9 wt % to about 12 wt %, or by a metal loading of 2.5 wt % to about 15 wt %, or by a metal loading of 5 wt % to about 15 wt %.

According to an aspect of the present disclosure, the porous zeolite monolith or the metal-doped porous zeolite monolith may have a total pore volume ($V_{total}$) of from about 0.25 cm$^3$/g to about 0.60 cm$^3$/g, or from about 0.2 cm$^3$/g to about 0.70 cm$^3$/g, or from about 0.1 cm$^3$/g to about 0.80 cm$^3$/g, or from about 0.2 cm$^3$/g to about 0.3 cm$^3$/g, or from about 0.15 cm$^3$/g to about 0.35 cm$^3$/g, or from about 0.1 cm$^3$/g to about 0.4 cm$^3$/g. In some aspects, the porous zeolite monolith or the metal-doped porous zeolite monolith may have a mesopore volume ($V_{meso}$) of from about 0.15 cm$^3$/g to about 0.35 cm$^3$/g, or from about 0.1 cm$^3$/g to about 0.4 cm$^3$/g, or from about 0.1 cm$^3$/g to about 0.5 cm$^3$/g, or from about 0.1 cm$^3$/g to about 0.2 cm$^3$/g, or from about 0.08 cm$^3$/g to about 0.25 cm$^3$/g. In some aspects, the the porous zeolite monolith or the metal-doped porous zeolite monolith may have a micropore volume ($V_{micro}$) of from about 0.10 cm$^3$/g to about 0.25 cm$^3$/g, or from about 0.05 cm$^3$/g to about 0.35 cm$^3$/g, or from about 0.08 cm$^3$/g to about 0.3 cm$^3$/g, or from about 0.09 cm$^3$/g to about 0.1 cm$^3$/g, or from about 0.08 cm$^3$/g to about 0.11 cm$^3$/g, or from about 0.05 cm$^3$/g to about 0.15 cm$^3$/g.

According to some aspects of the present disclosure, the porous zeolite monolith or the metal-doped porous zeolite monolith may comprise a plurality of pores, the pores having an average pore diameter from about 15 nanometers to about 75 nanometers, or from about 15 nanometers to about 550 nanometers, or from about 8 nanometers to about 100 nanometers, or from about 10 nanometers to about 40 nanometers, or from about 100 nanometers to about 2000 nanometers, or from about 10 nanometers to about 2000 nanometers.

In some aspects, the porous zeolite monolith or the metal-doped porous zeolite monolith may comprises a weak acid amount of from about 0.13 mmol/g to about 0.37 mmol/g and a strong acid amount of from about 0.3 mmol/g to about 0.65 mmol/g as measured by ammonia temperature programmed desorption. In another aspect, the porous zeolite monolith or the metal-doped porous zeolite monolith may comprise a weak acid amount of from about 0.1 mmol/g to about 0.4 mmol/g and a strong acid amount of from about 0.2 mmol/g to about 0.8 mmol/g as measured by ammonia temperature programmed desorption. In another aspect, the porous zeolite monolith or the metal-doped porous zeolite monolith may comprise a weak acid amount of from about 0.3 mmol/g to about 0.56 mmol/g and a strong acid amount of from about 0.07 mmol/g to about 0.16 mmol/g as measured by ammonia temperature programmed desorption. In another aspect, the porous zeolite monolith or the metal-doped porous zeolite monolith may comprise a weak acid amount of from about 0.25 mmol/g to about 0.6 mmol/g and a strong acid amount of from about 0.05 mmol/g to about 0.2 mmol/g as measured by ammonia temperature programmed desorption.

The presently disclosed compositions may be a catalyst for the catalytic cracking of alkanes to produce light olefins, and/or a catalyst for the catalytic conversion of alkanes to light olefins, and/or a catalyst for the catalytic conversion of alkanes to light olefins and benzene, toluene, and xylene (BTX). In such cases, the light olefins may be selected from the group consisting of ethylene, propylene, butylene, and any combination thereof. In some aspects, the alkanes may be selected from the group consisting of light alkanes or $C_3$-$C_{15}$ alkanes. According to at least one aspect of the present disclosure, the alkane may be n-hexane.

According to at least one aspect of the present disclosure, a porous zeolite monolith composition for the catalytic cracking of alkanes is provided. The composition may comprise a HZSM-5 zeolite monolith comprising a MFI framework and a coating on at least a portion of the HZSM-5 zeolite monolith. The coating may comprise a silicoaluminophosphate with chabazite (SAPO-34) framework. The composition may be prepared layer by layer using a 3D printer such that the composition comprises a plurality of micropores and a plurality of mesopores. The micropores may have a diameter of greater than 15 nanometers and the mesopores may have a diameter of from 2 nanometers to 15 nanometers. The composition may be characterized by a selectivity to light olefins of at least about 50.0% at a temperature of 650° C., or may be characterized by a selectivity to light olefins of at least about 53.0% at a temperature of 650° C. The composition may comprise a total pore volume ($V_{total}$) of from about 0.25 cm$^3$/g to about 0.60 cm$^3$/g or from about 0.2 cm$^3$/g to about 0.35 cm$^3$/g. The composition may also comprise a mesopore volume ($V_{meso}$) of from about 0.15 cm$^3$/g to about 0.30 cm$^3$/g or from about 0.15 cm$^3$/g to about 0.25 cm$^3$/g. The composition may also comprise a micropore volume ($V_{micro}$) of from about 0.10 cm$^3$/g to about 0.15 cm$^3$/g or from about 0.08 cm$^3$/g to about 0.13 cm$^3$/g.

The composition comprising a HZSM-5 zeolite monolith comprising a MFI framework and a coating, may further comprise a plurality of pores, the pores having an average pore diameter from about 15 nanometers to about 75 nanometers, or from about 15 nanometers to about 550 nanometers. The composition may also comprise a weak acid amount of from about 0.25 mmol/g to about 0.37 mmol/g and a strong acid amount of from about 0.2 mmol/g to about 0.32 mmol/g as measured by ammonia temperature programmed desorption.

According to at least one aspect of the present disclosure, a porous zeolite monolith composition for the catalytic cracking of alkanes is provided. The composition may comprise a HY zeolite monolith comprising a FAU framework a coating on at least a portion of the HY zeolite monolith. The coating may comprise a silicoaluminophosphate with chabazite (SAPO-34) framework. The composition may be prepared layer by layer using a 3D printer such that the composition comprises a plurality of micropores and a plurality of mesopores. The micropores may have a diameter of greater than 15 nanometers and the mesopores may have a diameter of from 2 nanometers to 15 nanometers. The composition may be characterized by a selectivity to light olefins of at least about 55.0% at a temperature of 600° C. or a selectivity to light olefins of at least about 57.0% at a temperature of 600° C. The composition may also be characterized by a selectivity to benzene, toluene, and xylene (BTX) of at least about 27.5% at a temperature of 600° C.

The porous zeolite monolith composition comprising a HY zeolite monolith comprising a FAU framework and a coating may further comprise a total pore volume ($V_{total}$) of from about 0.25 cm$^3$/g to about 0.60 cm$^3$/g, or from about 0.25 cm$^3$/g to about 0.35 cm$^3$/g. The composition may also have a mesopore volume ($V_{meso}$) of from about 0.15 cm$^3$/g to about 0.30 cm$^3$/g or from about 0.15 cm$^3$/g to about 0.25 cm$^3$/g. The composition may also have a micropore volume ($V_{micro}$) of from about 0.10 cm$^3$/g to about 0.25 cm$^3$/g or from about 0.08 cm$^3$/g to about 0.13 cm$^3$/g. The composition may also have a plurality of pores, the pores having an average pore diameter from about 15 nanometers to about 75 nanometers, or an average pore diameter from about 15 nanometers to about 550 nanometers. The composition may also comprise a weak acid amount of from about 0.1 mmol/g to about 0.25 mmol/g and a strong acid amount of from about 0.15 mmol/g to about 0.30 mmol/g as measured by ammonia temperature programmed desorption.

According to at least one aspect of the present disclosure, a metal-doped porous zeolite monolith composition for the catalytic cracking of alkanes is provided. The composition may comprise a ZSM-5 zeolite monolith comprising a MFI framework where the the ZSM-5 zeolite monolith comprises a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof. The composition may be prepared layer by layer using a 3D printer such that the composition comprises a plurality of micropores and a plurality of mesopores. The micropores may have a diameter of greater than 15 nanometers and the mesopores may have a diameter of from 2 nanometers to 15 nanometers. The composition may comprise from about 1 wt % to about 20 wt % metal content, or from about 2.5 wt % to about 12 wt % metal content, or from about 5 wt % to about 10 wt % metal content, or from about 9 wt % to about 12 wt % metal content, or from about 2.5 wt % to about 15 wt % metal content, or from about 5 wt % to about 15 wt % metal content. The composition may also comprise a total pore volume ($V_{total}$) of from about 0.2 cm$^3$/g to about 0.3 cm$^3$/g. The composition may further comprise a mesopore volume ($V_{meso}$) of from about 0.1 cm$^3$/g to about 0.2 cm$^3$/g and/or a micropore volume ($V_{micro}$) of from about 0.08 cm$^3$/g to about 0.10 cm$^3$/g.

The metal-doped porous zeolite monolith composition may also comprise a plurality of pores, the pores having an average pore diameter from about 8 nanometers to about 75 nanometers or an average pore diameter from about 8 nanometers to about 2000 nanometers. The composition may further comprise a weak acid amount of from about 0.3 mmol/g to about 0.6 mmol/g and a strong acid amount of from about 0.05 mmol/g to about 0.20 mmol/g as measured by ammonia temperature programmed desorption.

According to at least one aspect of the present disclosure, a method for preparing a porous zeolite monolith catalyst for the catalytic cracking of alkanes is provided. The method may include generating, using a 3D printer, a porous zeolite monolith catalyst from a zeolite paste by layer by layer deposition. The zeolite paste may comprise a zeolite powder, a binder, a plasticizer, and water. The binder may comprise bentonite clay and the plasticizer may comprise methyl cellulose. The zeolite powder may be selected from the group consisting of the hydrogen form of ZSM-5 zeolite (HZSM-5) and the hydrogen form of Y zeolite (HY, CBV780, SiO2/Al2O3=80). The zeolite paste may comprise a metal oxide precursor. In such cases, the metal oxide precursor may be a transition metal oxide precursor. The metal oxide precursor may also be selected from the group consisting of $Cr(NO_3)_3 \cdot 9H_2O$, $Cu(NO_3)_2 \cdot 2.5H_2O$, $Ni(NO_3)_2 \cdot 6H_2O$, and $Y(NO_3)_3 \cdot 6H_2O$.

The zeolite paste may comprise a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof. The zeolite paste may also comprises an aqueous nitrate solution comprising a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof. In some instances, the zeolite paste may comprise 87.5 wt % zeolite powder, 10 wt % binder, and 2.5 wt % plasticizer. In some instances, the zeolite monolith may be generated such that the zeolite monolith comprises a honeycomb-like structure. The zeolite monolith may also be generated such that the zeolite monolith comprises a plurality of interconnected channels. In some cases, the zeolite monolith may be generated such that the zeolite monolith comprises a plurality of micropores and a plurality of mesopores, the micropores having a diameter of greater than 15 nanometers and the mesopores having a diameter of from 2 nanometers to 15 nanometers.

In at least some instances, the method may further include forming a coating on the porous zeolite monolith catalyst. The coating may comprise a silicoaluminophosphate with chabazite (SAPO-34) framework. The coating may be formed by a secondary growth method. In such cases, the secondary growth method may include preparing a plurality of SAPO-34 seeds, contacting the generated porous zeolite monolith catalyst with the SAPO-34 seeds to form a seeded porous zeolite monolith catalyst, and contacting the seeded porous zeolite monolith catalyst with a SAPO-34 synthesis solution to form a SAPO-34 coating on the porous zeolite monolith catalyst. The SAPO-34 seeds may be prepared by mixing aluminum isopropoxide, colloidal silica, tetraethylammonium hydroxide, and phosphoric acid. The SAPO-34 synthesis solution may comprise a mixture of aluminum isopropoxide, colloidal silica, tetraethylammonium hydroxide, and phosphoric acid.

According to at least one aspect of the present disclosure, a method for the catalytic cracking of alkanes is provided. The method may include contacting an alkane with any of the presently disclosed zeolite monolith catalyst compositions. The contacting an alkane with a catalyst may occur at a temperature of from about 600° C. to about 650° C., or from about 200° C. to about 850° C., or from about 400° C. to about 800° C. The method may further include regenerating the catalyst a plurality of times by heating the catalyst to a temperature of up to 760° C. The catalyst used in the method may be characterized by a 98% or greater conversion of n-hexane at 650° C. after two regeneration cycles. The catalyst used in the method may exhibit a selectivity to light olefins of at least 50.0% at a temperature of 650° C., or a selectivity to light olefins of at least 53.0% at a temperature of 650° C., or a selectivity to light olefins of at least 55.0% at a temperature of 600° C., or a selectivity to light olefins of at least 57.0% at a temperature of 600° C. The catalyst used in the method may exhibit a selectivity to benzene, toluene, and xylene (BTX) of at least 27.5% at a temperature of 600° C. The alkanes used in the method may be selected from the group consisting of light alkanes or the group consisting of $C_3$-$C_{15}$ alkanes. In at least some instances, the alkane used in the method is n-hexane.

EXAMPLES

Example 1

Preparation of 3D-Printed Monolith

Ammonia-ZSM-5 powder (CBV 5524G, Zeolyst, SiO$_2$/Al$_2$O$_3$=50) was calcined at 550° C. for 6 h first. The resultant hydrogen form of ZSM-5 zeolite (HZSM-5) and Y zeolite (HY, CBV780, $SiO_2/Al_2O_3$=80) were used as the pristine zeolite powders for 3D printing of the monolithic catalysts. In the next step, approximately 87.5 wt. % zeolite was mixed with 10 wt. % bentonite clay which acted as the binder using an agitator (Model IKA-R25). Sufficient water was then added and stirred with the mixture to get a homogeneous slurry. The paste with extrudable viscosity and moisture was obtained after adding 2.5 wt. % methyl cellulose, as a plasticizer, with sufficient agitation. The aqueous paste was then transferred to a 10 mL syringe (Techcon Systems) carefully to prevent air voids or unfilled intervals. A nozzle with 0.60 mm in diameter was installed on the syringe for the dispensing of the paste. The fabrication of the monolithic zeolite catalysts was performed on a lab-scale 3D printer (Geeetech). The printing paths were programmed by AutoCAD software and coded by Slic3r. The paste was dispensed and deposited on an alumina substrate in layer-by-layer manner to generate honeycomb-like monoliths. The HZSM-5 and HY monoliths were noted as "ZM" and "YM" respectively while the pristine powder zeolites were noted as "ZP" and "YP".

Example 2

Growth of SAPO-34 on Monolith

Firstly, SAPO-34 seeds were produced using a mixture of aluminum isopropoxide ($Al(i-C_3H_7O)_3$, Simga-Aldrich), colloidal silica (40 wt %, SNOWTEX-ZL), tetraethylammonium hydroxide (TEAOH, 40 wt %, Simga-Aldrich), and $H_3PO_4$ (85 wt %, Simga-Aldrich) with molar ratio of 1.0 $Al_2O_3$:0.6 $P_2O_5$:0.6 $SiO_2$:6.0 TEAOH: 111 $H_2O$. Hydrothermal treatment was carried out in a 100 mL Teflon-lined stainless steel autoclave (Parr Instrument) at 180° C. for 3 h. The product was centrifuged and washed for three times to obtain SAPO-34 seeds followed by drying at 80° C. overnight. The 3D-printed monoliths, obtained according to Example 1, were immersed in the water suspension of 1.0 wt % SAPO-34 seeds, and then were shaken gently for 5 min. The seeded monoliths were lifted out of the suspension and dried at 80° C. overnight. Another synthesis solution with the molar ratio of 0.85 $Al_2O_3$:1 $P_2O_5$:0.3 $SiO_2$:2.0 TEAOH: 155 $H_2O$ was prepared using the above-mentioned chemicals. The seeded monoliths together with the solution were transferred to the Teflon-lined stainless steel autoclaves for hydrothermal treatment at 220° C. for 6 h. The obtained monoliths were washed with deionized water, dried overnight and calcined at 550° C. to remove template. The loading of SAPO-34 on ZM and YM were 4.9 wt. % and 11.2% wt. % respectively. SAPO-34 grown on HZSM-5 monolith (SZM) and SAPO-34 grown on HY monolith (SYM) were noted with an additional "S" prefix indicating the presence of SAPO-34 crystals. Various 3D-printed monolith samples with two different diameters (10 mm and 20 mm) were fabricated, as displayed in FIG. 1.

Example 3

Characteristics of Monolithic Catalysts

The monolithic catalysts obtained in Examples 1 and 2 were characterized using X-ray diffraction (XRD), scanning electron microscopy (SEM), $N_2$ physisorption/Brunauer-Emmett-Teller (BET), temperature-programmed desorption of ammonia ($NH_3$-TPD), and thermogravimetric analysis-differential thermal analysis (TGA-DTA). X-ray diffraction (XRD) spectra were obtained with a PANalytical X'Pert Multipurpose X-ray Diffractometer operated at 40 kV and 40 mA with Cu-Kα1 radiation. The scan angle (2θ) range was from 5° to 50° at a rate of 2.0° $min^{-1}$. Scanning electron microscopy (SEM) images were captured with a field-emission scanning microscope (Hitachi S-4700). Samples were fixed on a pin stub using carbon paste coated with Au/Pd. $N_2$ physisorption measurements were carried out with a Micromeritics 3Flex surface characterization analyzer at 77K. Before the measurements, all samples were degassed at 300° C. for 6 h. Textural properties including total surface area, external surface area and pore size distribution were measured using Brunauer-Emmett-Teller (BET) equation, t-plot and Barrett-Joyner-Halenda (BJH) methods respectively. The acid properties were measured by temperature-programmed desorption of ammonia ($NH_3$-TPD) using Micromeritics 3Flex analyzer. $NH_3$ adsorption was performed under a flow of 5 vol % $NH_3$/He. The desorption of $NH_3$ was measured from 100° C. to 600° C. at a constant heating rate of 10° C. $min^{-1}$. A mass spectroscopy (MicrotracBEL, BELMass) was used to detect the quantity of $NH_3$ desorption. To analyze the coke formation in the spent catalysts after n-hexane cracking, thermogravimetric analysis-differential thermal analysis (TGA-DTA) was carried out from 30° C. to 900° C., at a rate of 10° C./min using TGA (Model Q500, TA Instruments) in a 60 mL $min^{-1}$ air flow.

Figure 2:
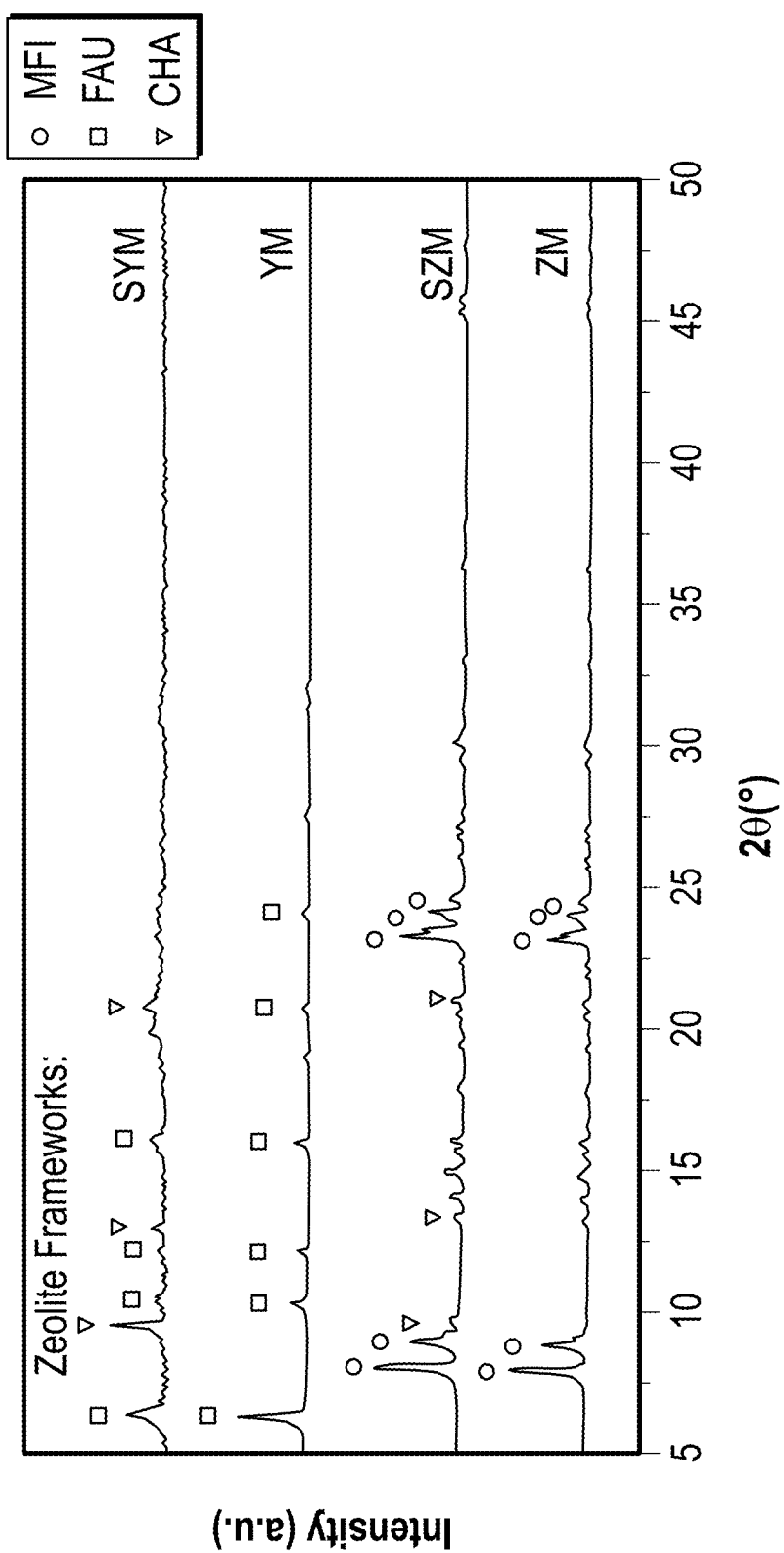
FIG. 2 is an illustration showing the X-ray diffraction (XRD) patterns for the monolithic catalysts obtained according to Examples 1 and 2, according to an exemplary embodiment of the present disclosure.
Figure 3B:
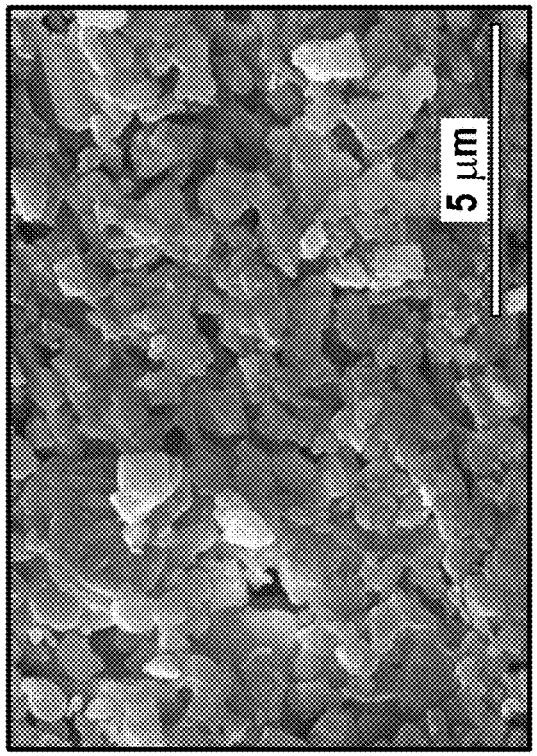
FIGS. 3A-3D are scanning electron microscope (SEM) micrographs of some monoliths obtained according Examples 1 and 2, according to an exemplary embodiment of the present disclosure.
Figure 3D:
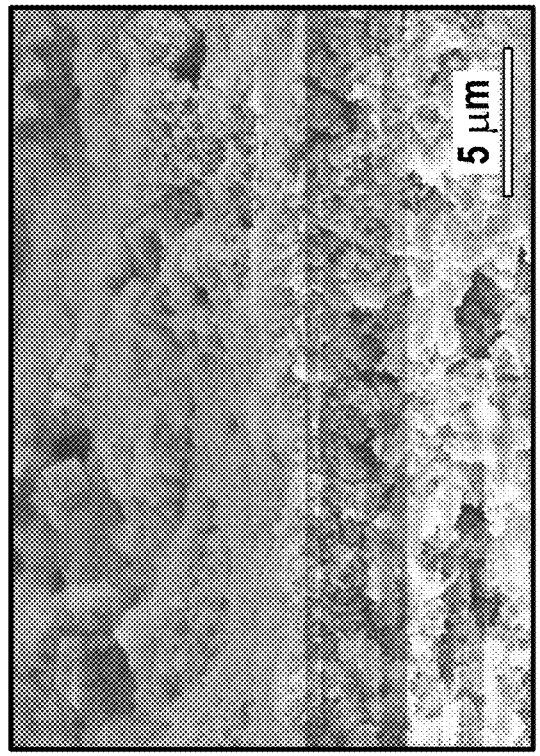
Figure 3A:
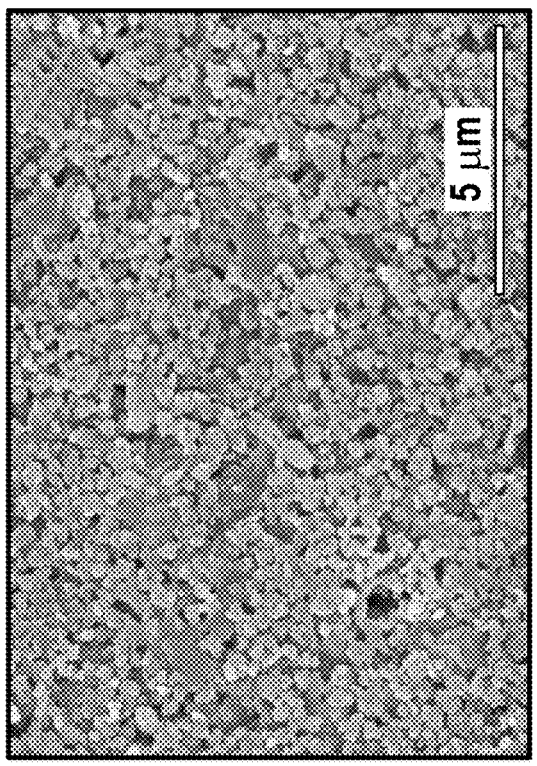
Figure 3C:
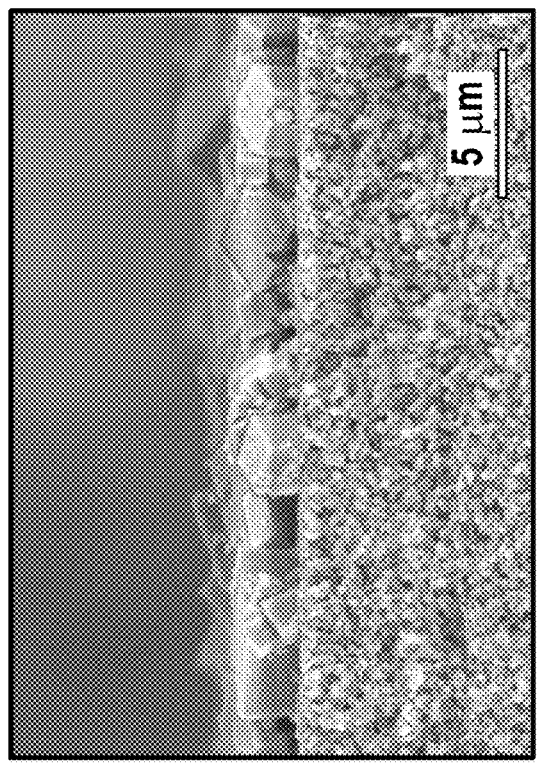

The XRD patterns of all monolith samples are shown in FIG. 2. ZM showed typical MFI framework characteristic peaks at 2θ=7.96°, 8.88°, 23.2°, 23.3° and 24.0° corresponding to (101), (200), (501), (341) and (303) planes respectively. Additionally, the peaks at 2θ=9.7°, 13.3° and 21.0° were observed on SZM and these peaks reflect the CHA framework of SAPO-34 crystal growth. Similarly, YM displayed characteristic peaks of FAU zeolite at 2θ=6.3°, 10.3°, 12.1°, 15.9°, 20.8° and 24.1° which attributed to (111), (220), (311), (331), (440) and (533) planes respectively. SYM retains most of characteristic peaks of HY zeolite but with weaker intensity. Additional sharp peaks at 2θ=9.7°, 13.3° and 21.0° indicated the formation of SAPO-34 crystal on the zeolite HY monolith surface. Zeolite HY with FAU framework consists of cages that can include spherical molecules of 1.12 nm in diameter and channels with maximum 0.74 nm diffusion ability, whereas the cages and channels of HZSM-5 with MFI framework are only 0.64 nm and 0.45 nm, much smaller than that of FAU. In our synthesis, when the growth of SAPO-34 on monolith was performed in the synthesis solution, the molecules of silica source, alumina source and template have more access to HY cages than HZSM-5. With proper crystallization condition, SAPO-34 crystals might grow in the FAU cages and undermined the original FAU framework. This possibility leads to the decrease in FAU peaks intensity. This explanation can also be verified by the fact that the surface area and pore volume of SYM are dramatically smaller than those of YM while the difference between SZM and ZM are mediocre, as can be seen later.

SEM images are presented in FIG. 3A-3D showing the morphology of the monolith samples. The comparison between ZM and YM under the same scale indicated that the sizes of the zeolite particles within HY monolith are generally larger than HZSM-5 monolith. Both monoliths possessed scattered mesopores on the surfaces which were generated by the removal of methyl cellulose after calcination. After grown with SAPO-34, cubic crystals were observed on both zeolite monolith surfaces, which are marked with red frames in FIGS. 3C and D. With attentive look around SAPO-34 crystals, nano-sized spherical SAPO- 34 seeds could also be found on both zeolite monoliths. These seeds were small enough to be attached to the walls of mesopores, as has been highlighted by the red circle on FIG. 3D. It is obvious that the proportion of undeveloped seeds on HY monolith surface were much more than on HZSM-5 monolith. It is possibly due to the superior surface area and porosity of YM which captured more seeds whereas the nutrient in the synthesis nutrient is limited.

Figure 4A:
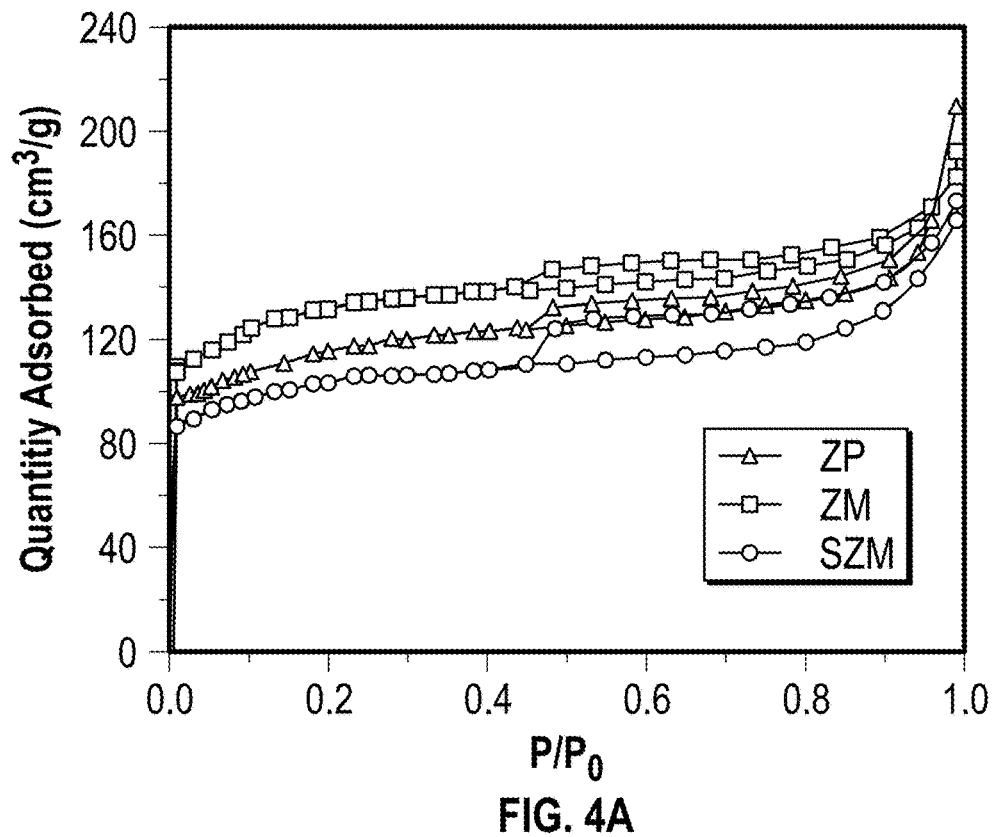
FIG. 4A depicts the $N_2$ physisorption isotherms of zeolite catalysts ZP, ZM, and SZM, according to an exemplary embodiment of the present disclosure.
Figure 4B:
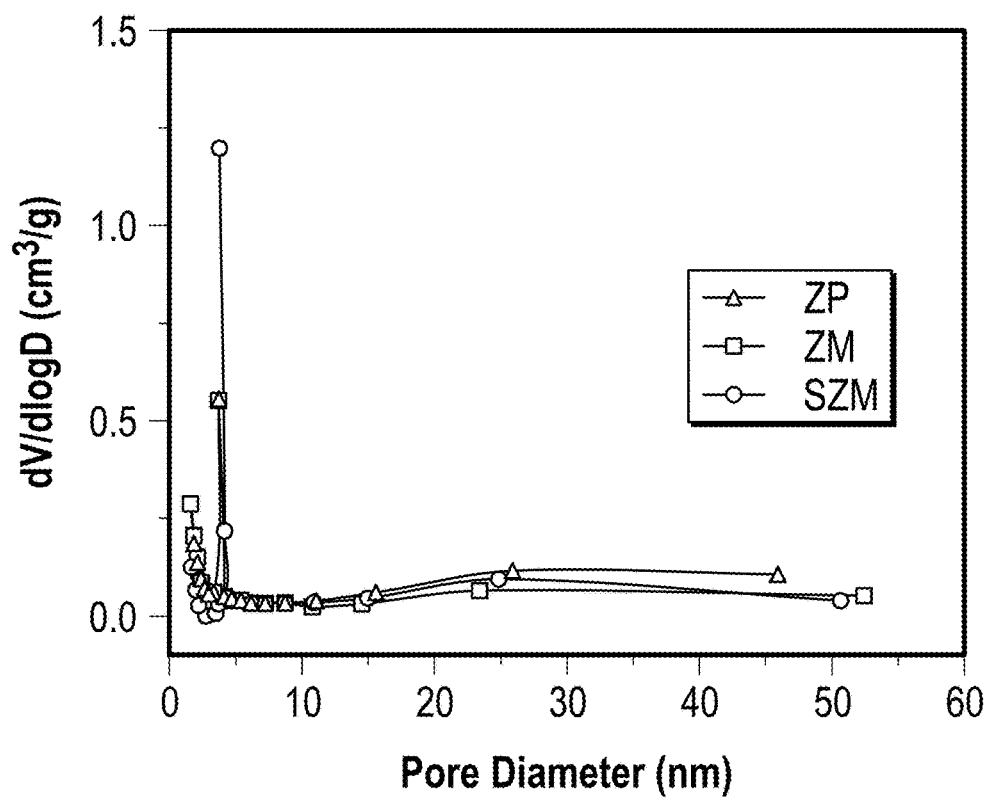
FIG. 4B depicts the pore size distribution of zeolite catalysts ZP, ZM, and SZM where the pore size distribution is derived from the Barrett-Joyner-Halenda (BJH) method using the desorption branch of the $N_2$ isotherm, according to an exemplary embodiment of the present disclosure.
Figure 4C:
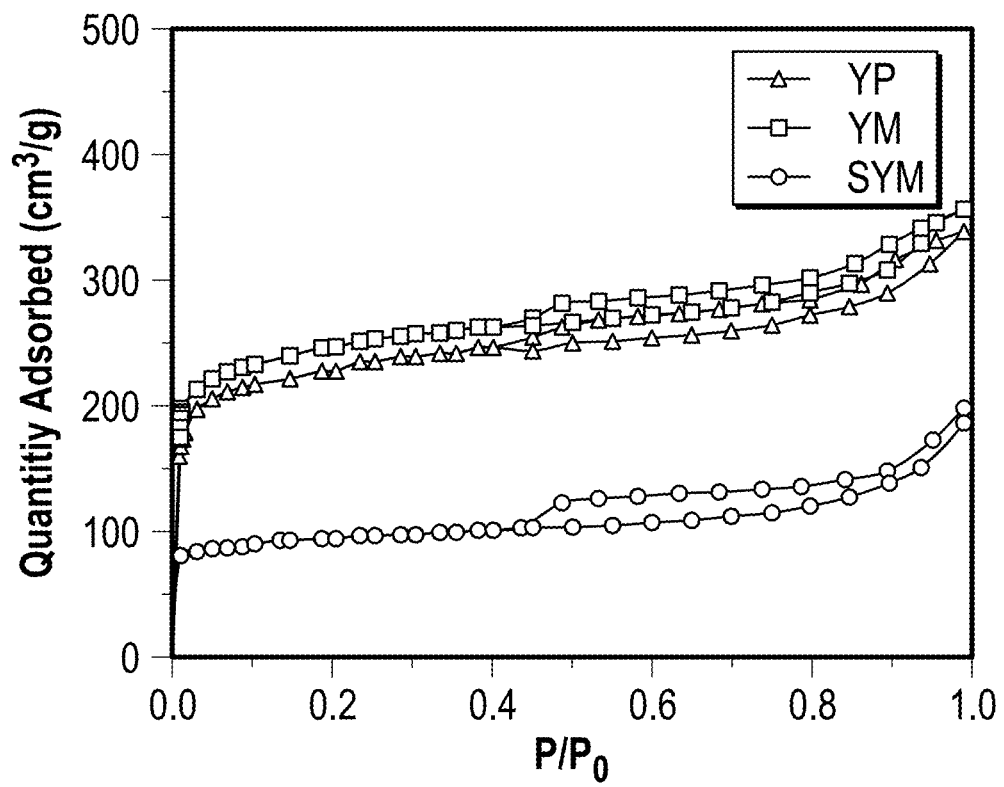
FIG. 4C depicts the $N_2$ physisorption isotherms of zeolite catalysts ZP, ZM, and SZM, according to an exemplary embodiment of the present disclosure.
Figure 4D:
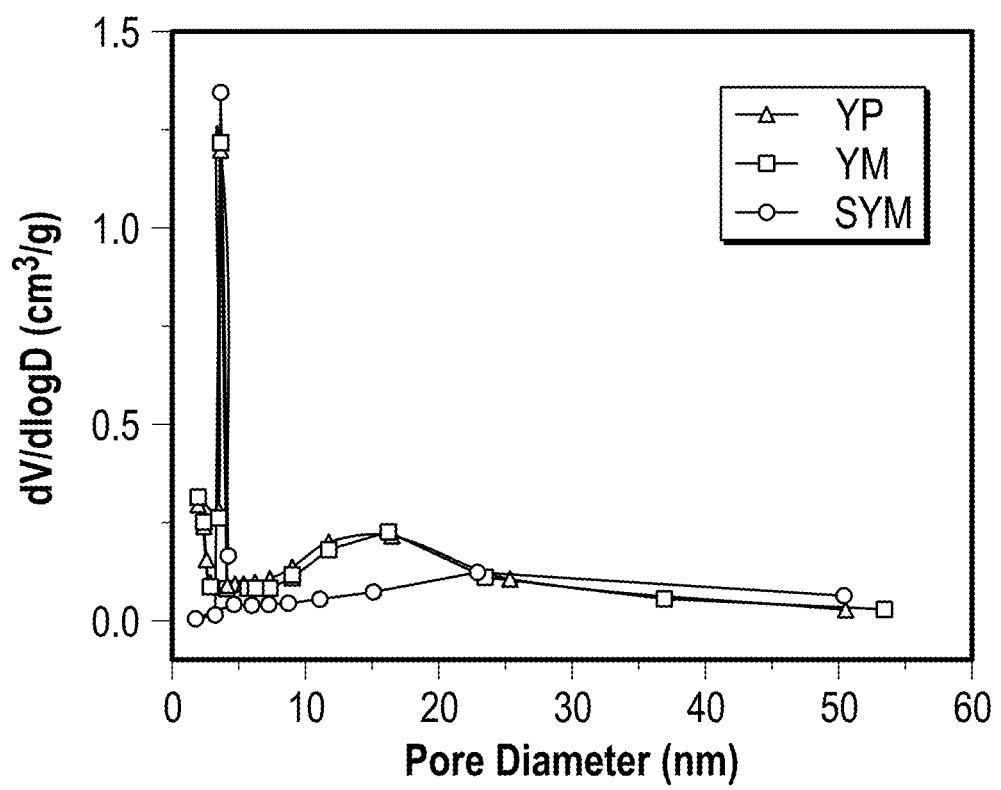
FIG. 4D depicts the pore size distribution of zeolite catalysts ZP, ZM, and SZM where the pore size distribution is derived from the Barrett-Joyner-Halenda (BJH) method using the desorption branch of the $N_2$ isotherm, according to an exemplary embodiment of the present disclosure.

Table 1 shows the physical properties of all the investigated monolith samples. Both the pristine HZSM-5 and HY zeolite powders bear mesopores intrinsically. The comparison between ZP and ZM indicated that HZSM-5 catalyst underwent a decrease in total surface area from 429 m² g⁻¹ to 373 m² g⁻¹ after fabrication into the monolith. The decline was mainly from the reduction in microporous surface area. This is due to the addition of less porous binder which diluted the zeolite. The same trend was also found in YP and YM pair. Although employment of the binder decreased the microporous volume, the total pore volume remained at the same level because of the creation of mesopores in the monolith, as discussed above. This matched the enhanced mesoporous volume values in Table 1 and the pore size distribution results in FIGS. 4B-4D. The generation of mesopores were found in both HZSM-5 and HY monoliths. Considering the 1.2 mm of channel dimension of honeycomb-like monoliths, measured by SEM images, the 3D printing fabrication render the zeolite monolith a macro-meso-microporous structure material. As the monoliths were coated with SAPO-34 crystals, both total surface area and pore volume declined due to pore clogging caused by SAPO-34 growth. It is worth mentioning that the volume of the pores below 2 nm in diameter of SYM is much smaller than that of YM, as shown in the inset figure of FIG. 4D. It verified the hypothesis that SAPO-34 crystals grew in the FAU cages and undermined the original FAU framework. The decline of pore volume at the sizes ranging from 10-25 nm could be attributed to the SAPO-34 seeds attached to walls of mesopores, as has been shown by the SEM image.

TABLE 1

Physical properties of the investigated samples obtained from nitrogen physisorption.

| samples | $S_{BET}^{a}$ (m² g⁻¹) | $S_{micro}^{b}$ (m² g⁻¹) | $S_{ext}$ (m² g⁻¹) | $V_{total}^{c}$ (cm³ g⁻¹) | $V_{micro}$ (cm³ g⁻¹) | $V_{meso}$ (cm³ g⁻¹) |
|---|---|---|---|---|---|---|
| ZP | 429 | 261 | 168 | 0.30 | 0.13 | 0.17 |
| ZM | 373 | 214 | 159 | 0.30 | 0.10 | 0.20 |
| SZM | 336 | 206 | 130 | 0.27 | 0.10 | 0.17 |
| YP | 795 | 492 | 303 | 0.55 | 0.25 | 0.30 |
| YM | 732 | 444 | 288 | 0.53 | 0.22 | 0.31 |
| SYM | 309 | 205 | 104 | 0.30 | 0.10 | 0.20 |

$^{a}S_{BET}$ was obtained by analyzing nitrogen adsorption data at 77 K in a relative vapor pressure ranging from 0.05 to 0.30.
$^{b}$Micropore area and micropore volume were determined using t-plot method.
$^{c}$Total pore volume was estimated based on the volume adsorbed at P/P$_o$ = 0.99.

Figure 5A:
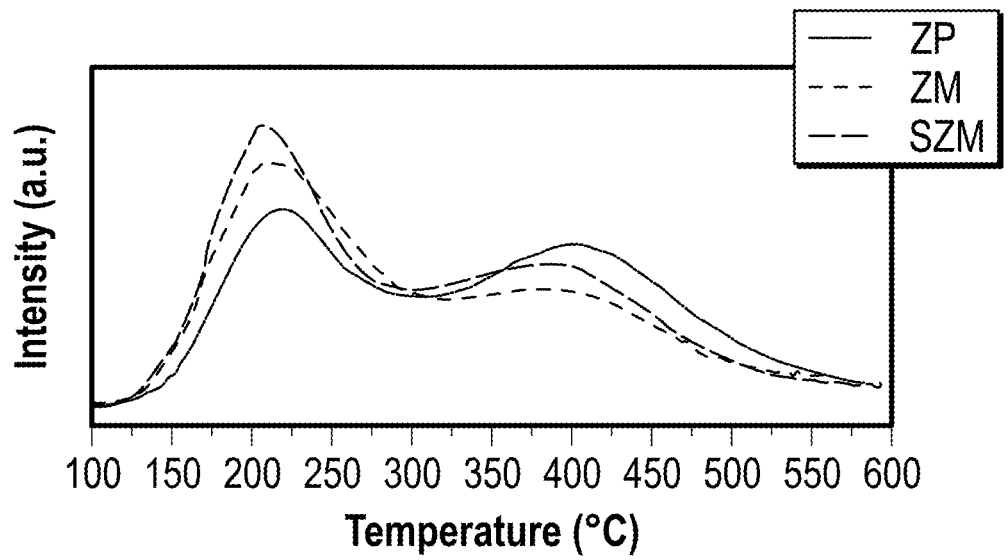
FIG. 5A depicts $NH_3$-TPD profiles of zeolite catalysts ZP, ZM, and SZM, according to an exemplary embodiment of the present disclosure.
Figure 5B:
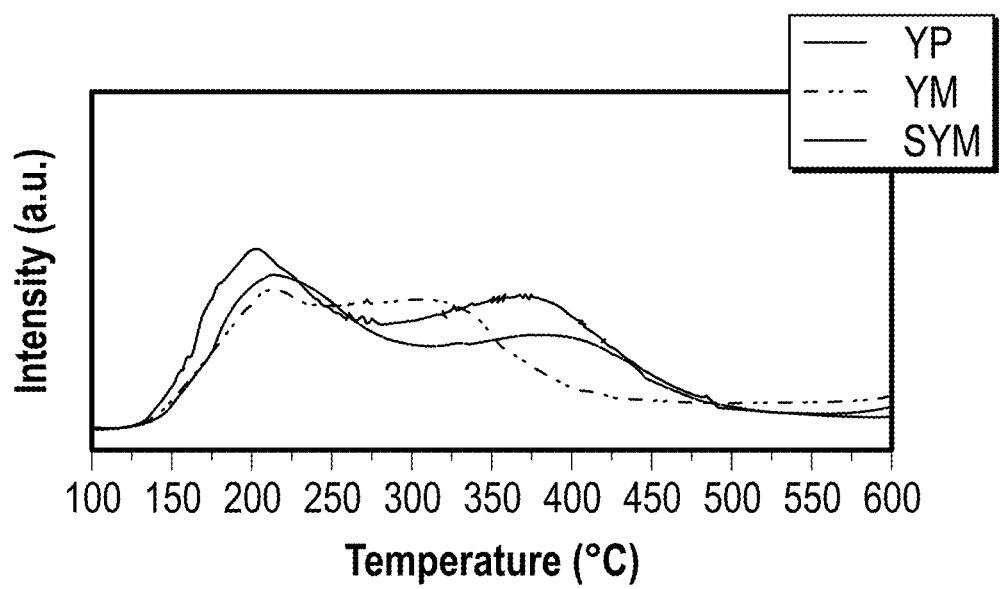
FIG. 5B depicts $NH_3$-TPD profiles of zeolite catalysts YP, YM, and SYM, according to an exemplary embodiment of the present disclosure.

The acidity of the catalysts was analyzed with the NH₃-TPD the patterns which are presented in FIG. 5 with the corresponding acid strength and acid sites amount date listed in Table 2. The HZSM-5 catalyst exhibited more total acid sites amount (ca. 0.57-0.63 mmol g⁻¹) than HY samples (ca. 0.32-0.49 mmol g⁻¹). For the powder and bare monolith catalysts in each group, the total quantity of acid sites estimated from desorbed ammonia were fairly similar and that of monoliths were slightly lower. As expected, the SAPO-34 coated monoliths exhibited much higher total acid sites amount due to the introduction of acidic SAPO-34. As can be observed from these results, both the formulation into monolith structure and the further coating with CHA framework zeolite have significant effect on the catalyst acid strength distribution, while effect varies with zeolite type. The formulation into monolith structure reduced the strong acid sites amount of HZSM-5 zeolite from 0.309 mmol g⁻¹ (ZP) to 0.204 mmol g⁻¹ (ZM) and enhanced weak acid sites amount from 0.268 mmol g⁻¹ to 0.365 mmol g⁻¹. On the other hand, the formulation of HY zeolite monolith increased the strong acid sites amount and decreased the weak acid sites. However, considering the dramatic shift of HY strong acid peak from 380° C. to 304° C., the overall acidity was actually moderated. The introduction of SAPO-34 increase strong acid sites amount of HZSM-5 from 0.204 mmol g⁻¹ (ZM) to 0.277 mmol g⁻¹ (SZM) and of HY from 0.189 mmol g⁻¹ (YM) to 0.259 mmol g⁻¹ (SYM).

TABLE 2

Acid strength and acid sites amount calculated from NH₃-TPD profiles.

| | Weak acid peak | | Strong acid peak | | Total |
|---|---|---|---|---|---|
| Sample | T (° C.) | Amount (mmol g⁻¹) | T (° C.) | Amount (mmol g⁻¹) | amount (mmol g⁻¹) |
| ZP | 217 | 0.268 | 403 | 0.309 | 0.577 |
| ZM | 214 | 0.365 | 378 | 0.204 | 0.569 |
| SZM | 208 | 0.352 | 381 | 0.277 | 0.629 |
| YP | 216 | 0.227 | 380 | 0.159 | 0.385 |
| YM | 211 | 0.132 | 304 | 0.189 | 0.322 |
| SYM | 201 | 0.231 | 371 | 0.259 | 0.490 |

Example 4

Catalytic Cracking of n-Hexane

The catalytic performance of the catalysts in both powder and monolith forms (obtained in Examples 1 and 2) were investigated in the conversion of n-hexane to light olefins at various reaction temperatures. A flow of nitrogen saturated with n-hexane at 30° C. was fed to a stainless steel packed-bed reactor. A mass flow controller (Brooks, 5850) was used to control the feed flow rate. About 0.3 g of each catalyst was tested under 600 and 650° C. at 1.01 bar in the tubular reactor with an internal diameter of 10 mm and a length of 300 mm. The weight hourly space velocity (WHSV) was kept at 5 h⁻¹ constantly. Before each run, the catalyst was activated in situ at 500° C. in nitrogen flow for 2 h. The products were analyzed on-line every 30 min using a gas chromatography (SRI 8610C) equipped with a flame ionized detector (GC-FID) connected to mxt-wax/mxt-alumina capillary column for hydrocarbons. Helium was used as the carrier gas. The effluent line of the reactor till GC injector was kept at 110° C. to avoid potential condensation of hydrocarbons.

The n-hexane conversion rates ($X_{n\text{-}hexane}$) as a function of time on stream are exhibited in FIG. 6. All catalysts showed enhanced activity in n-hexane conversion under higher reaction temperature. Moreover, although ZP showed slightly higher n-hexane conversion than ZM and SZM under both reaction temperatures at initial stages of the reaction, it experienced an obvious decline within 24 h on stream. The monolithic catalysts, ZM and SZM, displayed a stable n-hexane conversion during the investigated time on stream. It is generally believed that coke formation in zeolite catalysts is the cause of its deactivation. Factors such as external surface area, strong acid sites amount and acid site density influence the amounts of coked deposition. As discussed in the previous section, the strong acid sites amount of the monolith catalysts ZM and SZM are lower than that of ZP, leading to less deactivation by coke formation. It is apparent that the fabrication of monoliths, which possess diluting binder and monolith channels, decreased the acid sites density hence retarded the coking rate and extended the catalyst lifetime. The fact that SZM showed slightly higher n-hexane conversion than bare ZM is in agreement with $NH_3$-TPD data in which SAPO-34 growth enhanced the total acid sites amount of the monolith. Furthermore, the hierarchical zeolite monoliths with macro-meso-microporosity favored the mass transfer of the intermediates and products hence suppressed secondary reactions such as aromatics polymerization and reduced coke formation.

Figure 6A:
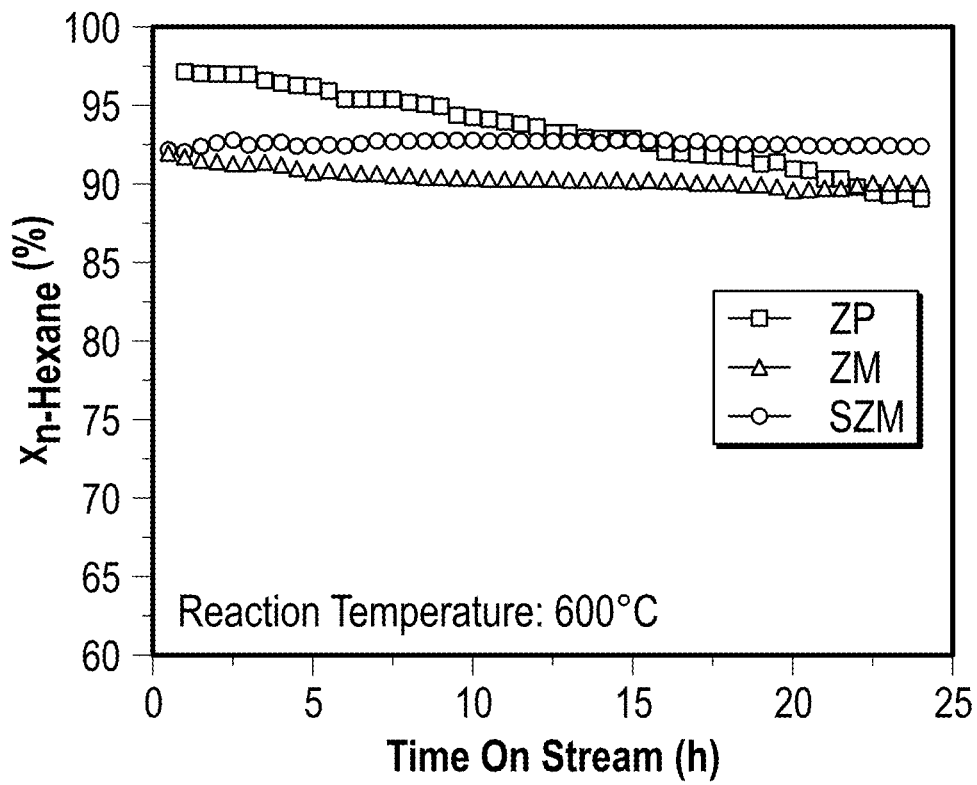
FIG. 6A depicts the conversion of n-hexane as a function of time on stream for zeolite catalysts ZP, ZM, and SZM at 600° C., where the reactant is n-hexane, WHSV is 5 $h^{-1}$, the time on stream is 24 h, and the pressure is 1.01 bar, according to an exemplary embodiment of the present disclosure.
Figure 6B:
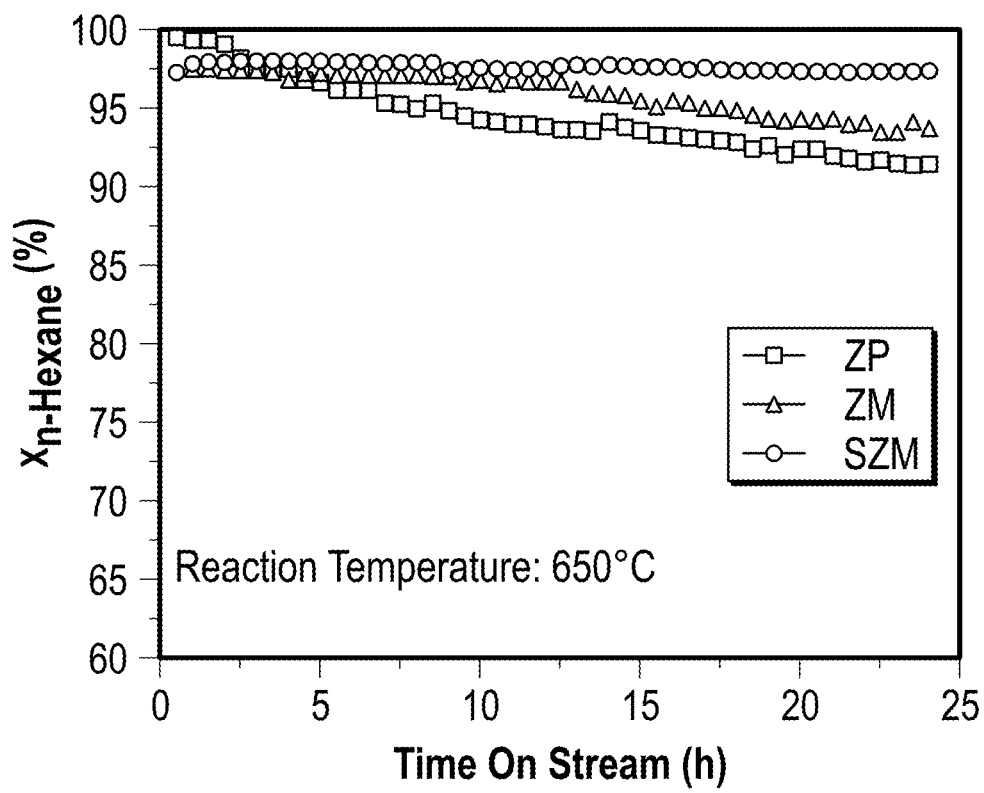
FIG. 6B depicts the conversion of n-hexane as a function of time on stream for zeolite catalysts ZP, ZM, and SZM at 650° C., where the reactant is n-hexane, WHSV is 5 h$^{-1}$, the time on stream is 24 h, and the pressure is 1.01 bar, according to an exemplary embodiment of the present disclosure.
Figure 6C:
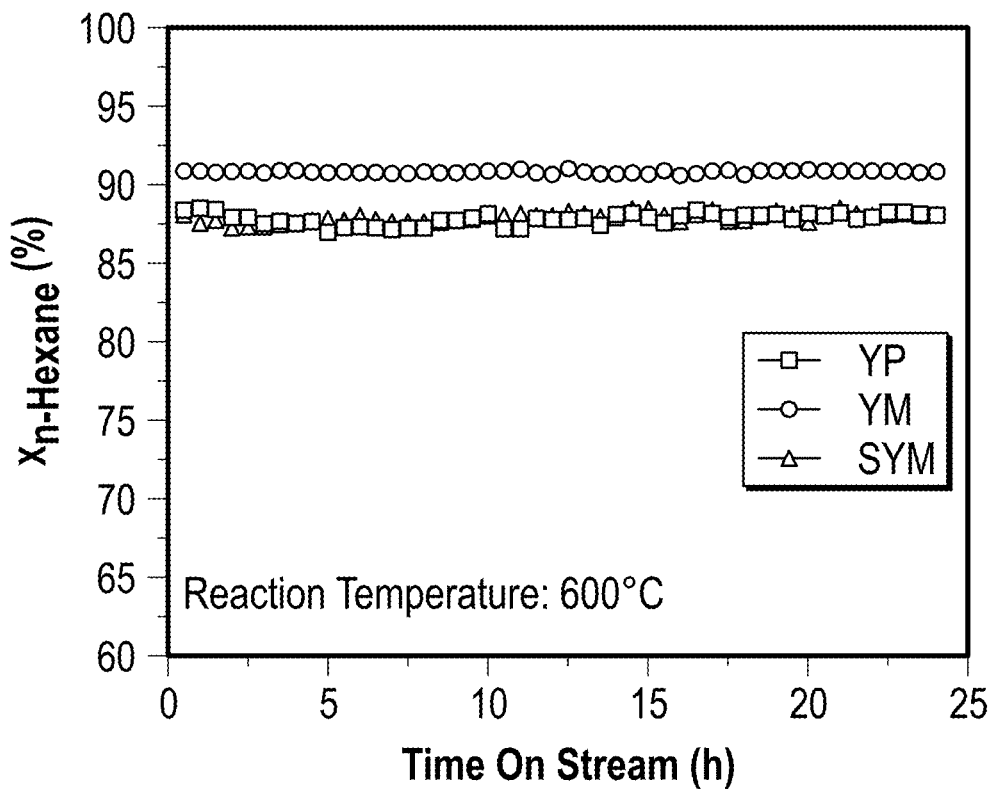
FIG. 6C depicts the conversion of n-hexane as a function of time on stream for zeolite catalysts YP, YM, and SYM at 600° C., where the reactant is n-hexane, WHSV is 5 h$^{-1}$, the time on stream is 24 h, and the pressure is 1.01 bar, according to an exemplary embodiment of the present disclosure.
Figure 6D:
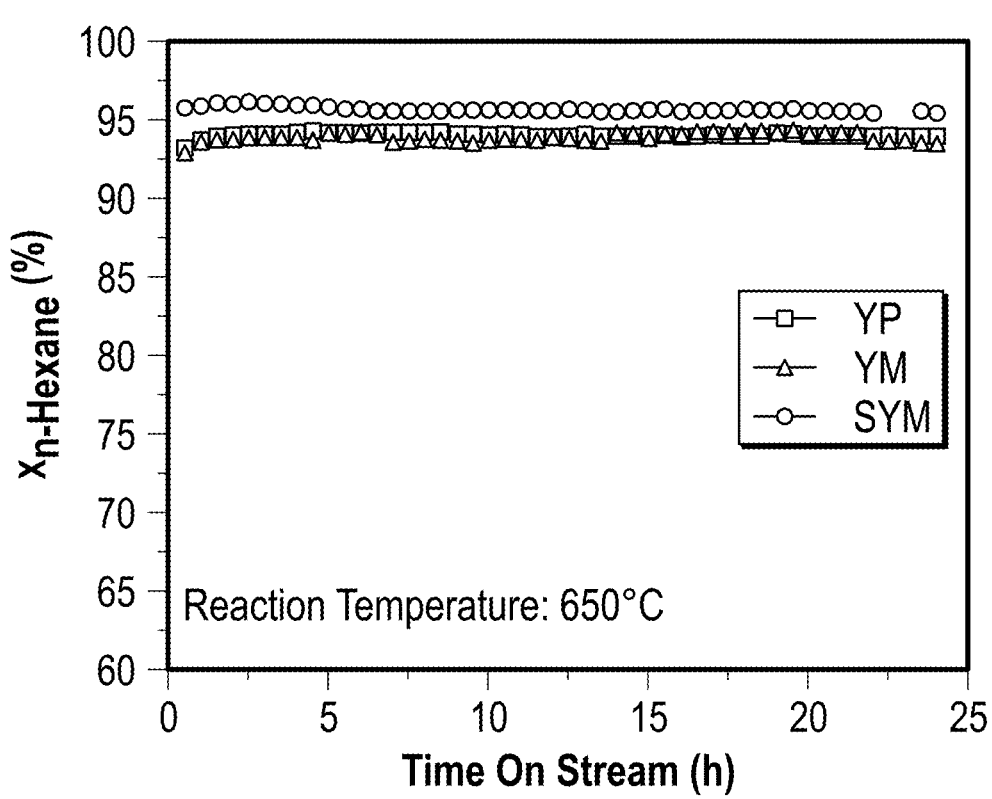
FIG. 6D depicts the conversion of n-hexane as a function of time on stream for zeolite catalysts YP, YM, and SYM at 650° C., where the reactant is n-hexane, WHSV is 5 h$^{-1}$, the time on stream is 24 h, and the pressure is 1.01 bar, according to an exemplary embodiment of the present disclosure.

In the case of HY zeolite, powder (YP) and bare monolith (YM) showed similar activity in n-hexane conversion at 600° C. and 650° C., as can be observed in FIGS. 6C and 6D respectively. The n-hexane conversion over HY zeolite monolith coated with SAPO-34 (SYM) was higher than the other two HY zeolite catalysts. This outstanding conversion rate could be attributed to the superior total acid sites amount by SAPO-34 growth. Unlike HZSM-5 zeolite catalyst, all HY catalysts, regardless of catalyst structure, retained their activity in n-hexane conversion within 24 h on stream. The comparison of the external surface area between ZP and YP could explain the remarkable stability of HY zeolite catalyst. It is typically considered that the coke formation mainly occurs on the external surface of the zeolite crystal. YP with an external surface area of 303 $m^2g^{-1}$, much higher than ZP with 168 $m^2g^{-1}$, suffered much less deactivation caused from coke deposition. In addition, HY zeolite framework bears cages and channels with much larger dimension than that of HZSM-5 zeolite, as discussed in previous sections. Larger space lessened the coke deposition which was confined in cages of zeolite crystals.

The products obtained from the n-hexane conversion over the investigated catalysts were found to be paraffin ($C_1$-$C_5$), olefins ($C_2^=$-$C_5^=$) and BTX (benzene, toluene, and xylene). FIG. 7A-D summarizes the selectivity to various hydrocarbons in three separate periods of the reaction: 1 h on stream, the initial period of the reaction; 10 h on stream, the medial period of the reaction; 24 h on stream, the final period of the reaction. To be conclusive, ethylene ($C_2^=$), propylene $C_3^=$ and butylene ($C_4^=$), known as light olefins, are stacked in an individual column and plotted along with BTX, paraffin and other hydrocarbons represented by assorted color. In each period of the reaction, catalysts are displayed and compared in the following order: powder zeolite, bare monolith and monolith with coated SAPO-34.

Figure 7A:
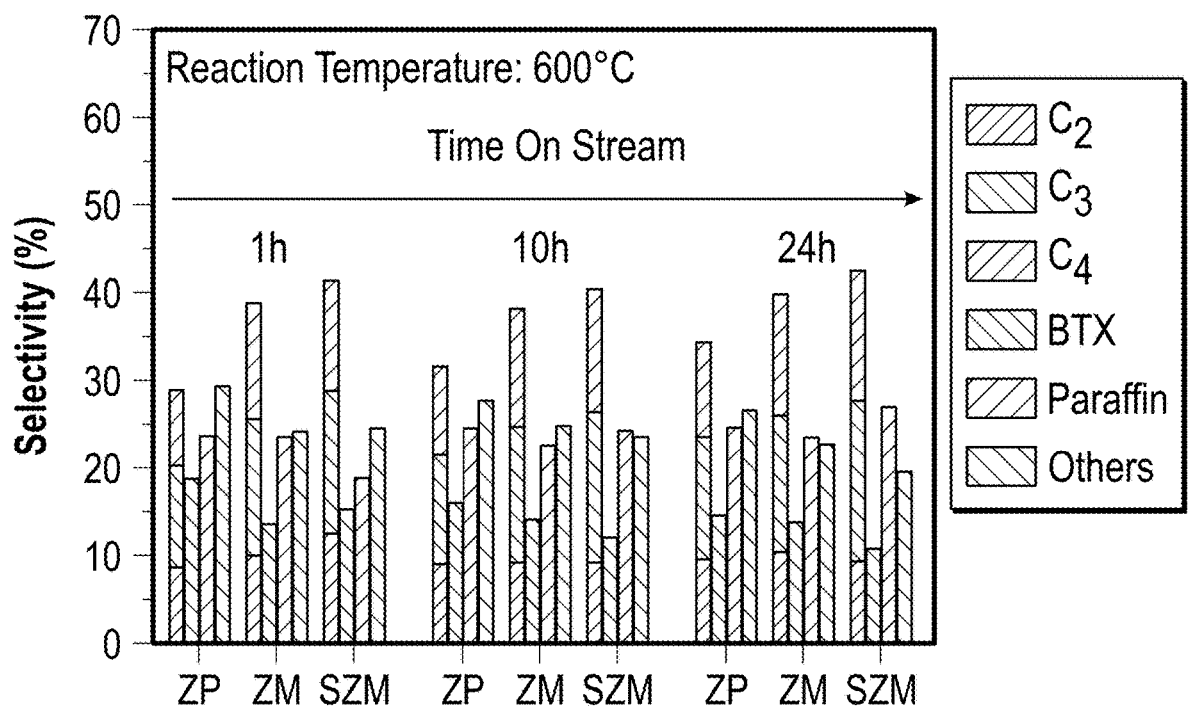
FIG. 7A depicts the product distribution for zeolite catalysts ZP, ZM, and SZM at 600° C., where the reactant is n-hexane, WHSV is 5 h$^{-1}$, the time on stream is 24 h, and the pressure is 1.01 bar, according to an exemplary embodiment of the present disclosure.
Figure 7B:
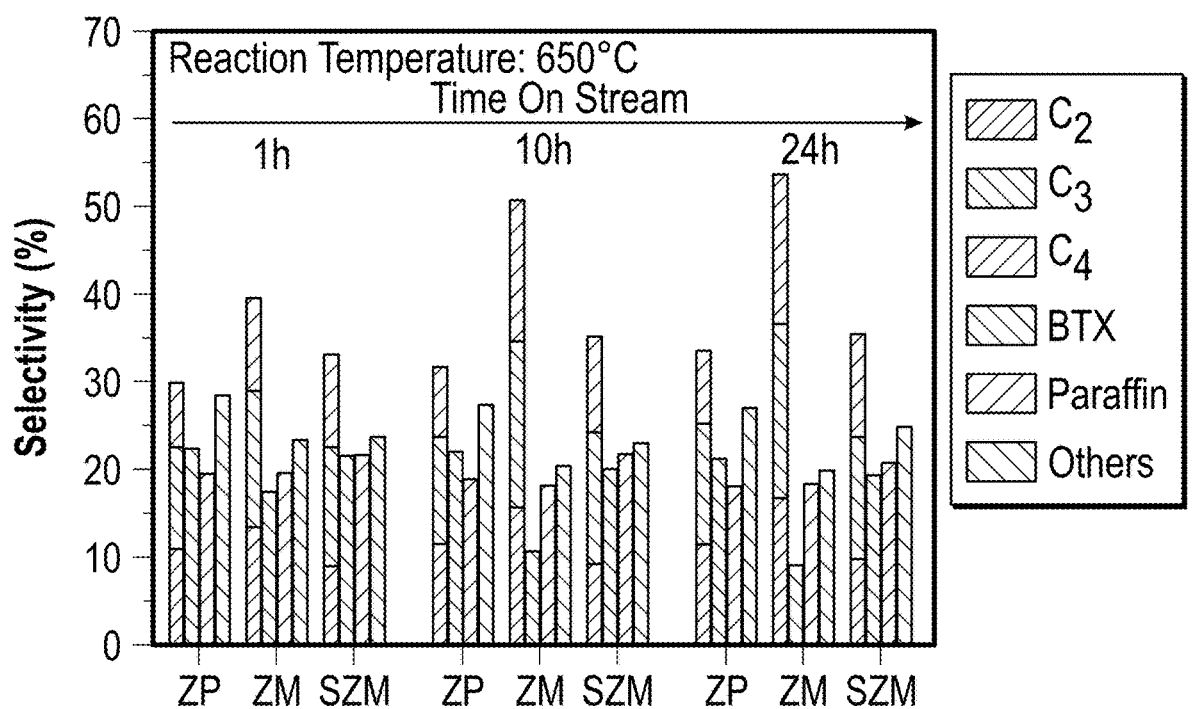
FIG. 7B depicts the product distribution for zeolite catalysts ZP, ZM, and SZM at 650° C., where the reactant is n-hexane, WHSV is 5 h$^{-1}$, the time on stream is 24 h, and the pressure is 1.01 bar, according to an exemplary embodiment of the present disclosure.
Figure 7C:
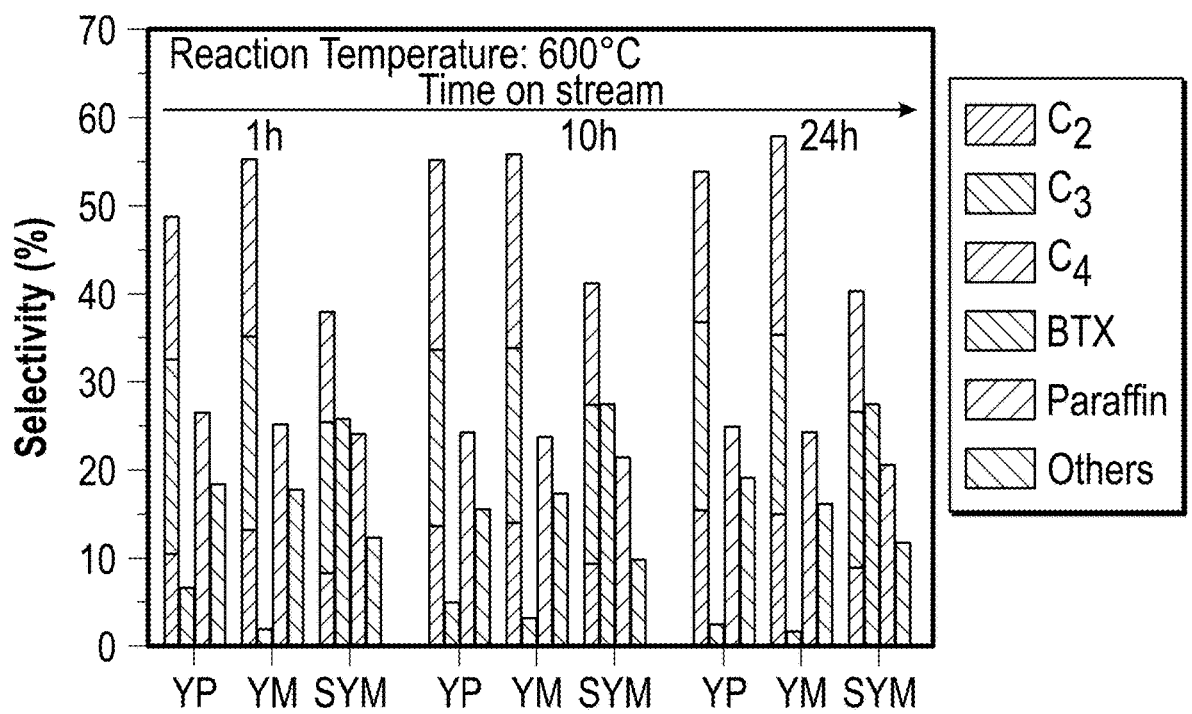
FIG. 7C depicts the product distribution for zeolite catalysts YP, YM, and SYM at 600° C., where the reactant is n-hexane, WHSV is 5 h$^{-1}$, the time on stream is 24 h, and the pressure is 1.01 bar, according to an exemplary embodiment of the present disclosure.
Figure 7D:
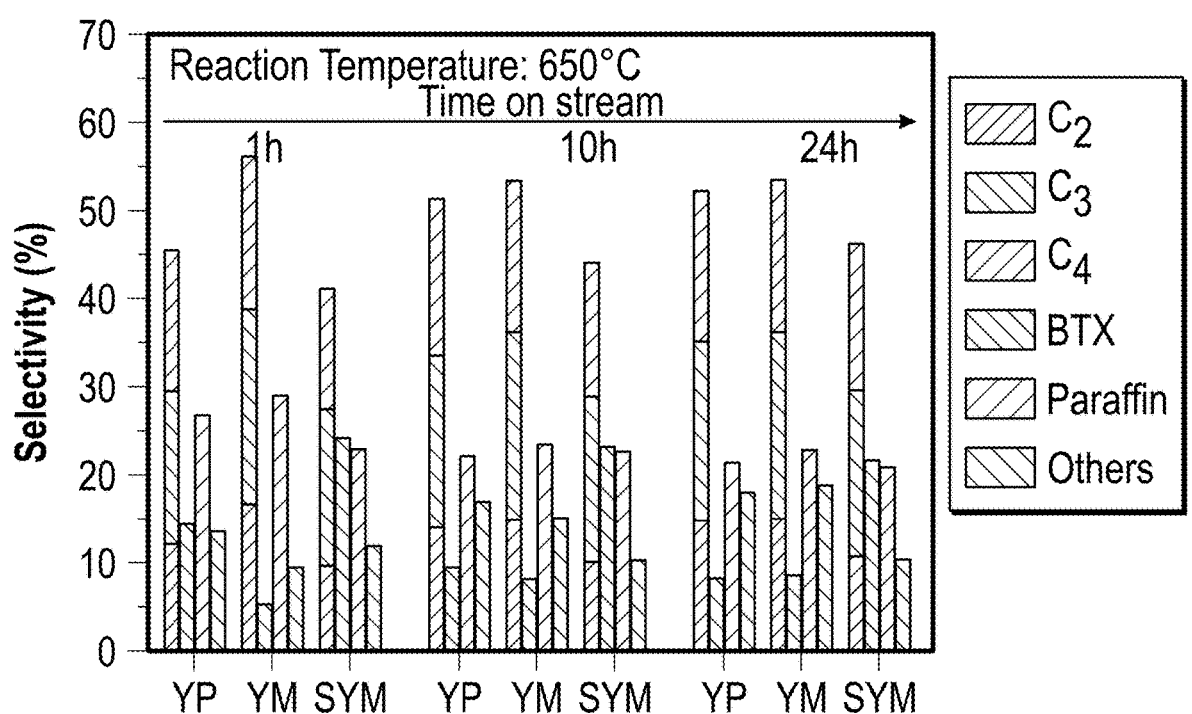
FIG. 7D depicts the product distribution for zeolite catalysts YP, YM, and SYM at 650° C., where the reactant is n-hexane, WHSV is 5 h$^{-1}$, the time on stream is 24 h, and the pressure is 1.01 bar, according to an exemplary embodiment of the present disclosure.

FIGS. 7A and 7B illustrate the product distribution over different HZSM-5 zeolite samples at 600° C. and 650° C. respectively. In all stages, bare monolithic HZSM-5 showed higher selectivity to light olefins and lower BTX selectivity than its powder counterpart (ZP), at both temperatures. It is well accepted that n-hexane cracking is initiated with the formation of carbenium ion and then undergoes β-scission to give carbenium ion of lower carbon number and light olefins. The successive reactions of these light olefins produce BTX. Javaid et al. reported that smaller acid concentration (total acid sites amount per unit mass) suppressed the formation of BTX. These findings match with the $NH_3$-TPD results: the acid sites amount decreased for monolith compared to powder sample. The same trend was also observed for HY powder (YP) and monolith catalysts. The highest selectivity to light olefins on HZSM-5 zeolite (53.0%) was found over ZM at 650° C. in 24 h on stream while the highest on HY zeolite (57.9%) was obtained at 600° C. in 24 h on stream. It is noteworthy that the BTX selectivity on YP and YM were significantly small. This could be related to the large channels of the FAU framework which provide plenty of room for the reaction and adequate diffusion for the light olefins so that aromatization was suppressed.

The effect of SAPO-34 growth on the products distribution varied with the reaction temperature, as well as the zeolite type. The presence of SAPO-34 on the monolith surface increased the light olefin selectivity and decreased BTX selectivity at 600° C. on HZSM-5 zeolite whereas a reverse trend was observed at 650° C. This could be explained by the fact that the aromatization of olefins on HZSM-5 is influenced by reaction temperature. High reaction temperature favors the formation of BTX from hydrocarbons of lower carbon number. At 650° C., boosted aromatization resulted in the reduction in light olefins and enhancement in BTX production. However, at 600° C. the acidity enhancement by SAPO-34 growth on the monolith might promote the production of light olefins, but further aromatization to BTX was thermodynamically limited. On HY zeolite monoliths, SAPO-34 growth dramatically increased the BTX selectivity compared to the bare sample. The significant improvement is the results of both surface property modification and the acidity enhancement. The highest BTX selectivity reached up to 27.5% over SYM at 600° C.

Figure 8:
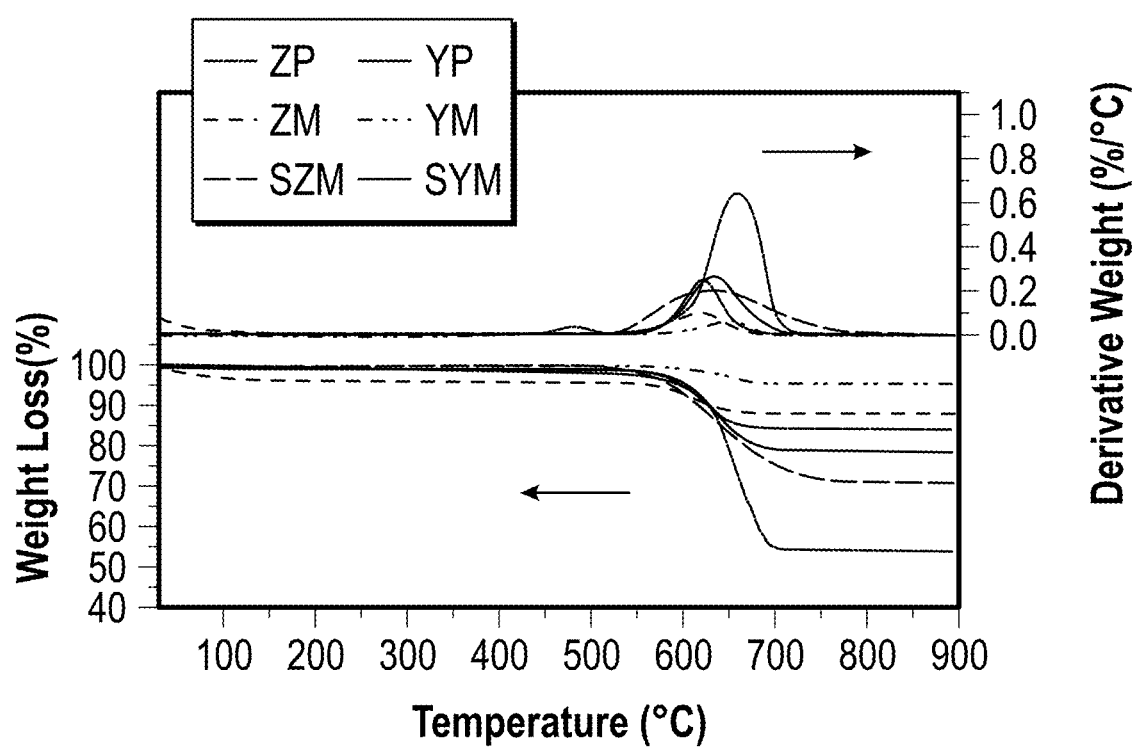
FIG. 8 depicts TGA (lower) and DTA (upper) profiles of the spent catalysts after n-hexane cracking at 650° C. for the zeolite catalysts, according to an exemplary embodiment of the present disclosure.

To verify the cause of catalyst deactivation and benefits of monolithic catalysts, TGA of the spent catalysts after 24 h of n-hexane cracking at 650° C. was carried out in the temperature range of 30-900° C. in a 60 mL $min^{-1}$ air flow. Both TGA and corresponding DTA profiles were plotted and displayed in FIG. 8. All catalysts exhibited a significant weight loss above 600° C. which represents the formation of 'hard coke' due to the activity on acid sites. A peak in DTA profile for HZSM-5 powder (ZP) was observed at lower temperature between 450 and 500° C. It is attributed to the 'soft coke' associated with the condensation and subsequent growth of coke precursor in the catalyst pore system. Owing to the relatively high acid sites amount as well as the restricted diffusion of intermediates and products in the confined cages and channels, the most severe coke formation was found in HZSM-5 powder. It was in agreement with the rapid deactivation of ZP therefore related the good performance of monolithic catalysts with their hierarchical porous structures.

Example 5

Preparation of Metal-Doped Porous Zeolite Monolith Catalysts

Bare 3D-printed ZSM-5 monoliths without metal modification were prepared according the method described in Example 1. Metal-doped ZSM-5 monoliths were prepared according to the same method, except that instead of deionized water, an aqueous nitrate solution with approximately 10 wt. % of metal content was added to the zeolite/bentonite mixture and shaken over night to get a homogenous slurry. It was determined that 5-10 wt. % metal loading is an optimum loading to positively affect the porosity and acidity of the zeolite. Lower metal loadings tend to lead to no obvious modification while higher metal loadings tend to cause too much pore clogging, framework damage, and negatively affect the zeolite properties. The rest of preparation steps were the same as bare ZSM-5 monolith preparation step. The bare ZSM-5 without modification was noted as ZM, whereas the samples with metal modification were noted as MeZM (Me=Cr, Cu, Ni, Y).

The pristine MFI zeolite powder used for making the paste was the commercial ammonia-ZSM-5 with the $SiO_2/Al_2O_3$ ratio of 50 (CBV 5524G, Zeolyst) which was calcined at 550° C. for 6 h to obtain HZSM-5. Methyl cellulose (Sigma-Aldrich) and bentonite clay (Sigma-Aldrich) were used as plasticizer and binder, respectively in the pastes. The transition metal oxide precursors including $Cr(NO_3)_3 \cdot 9H_2O$, $Cu(NO_3)_2 \cdot 2.5H_2O$, $Ni(NO_3)_2 \cdot 6H_2O$ and $Y(NO_3)_3 \cdot 6H_2O$ were all purchased from Sigma-Aldrich.

Example 6

Characterization of Metal-Doped 3D-Printed ZSM-5 Porous Zeolite Monolith Catalysts The zeolite catalysts obtained in Example 5 were characterized using X-ray diffraction (XRD), scanning electron microscopy (SEM), $N_2$ physisorption/Brunauer-Emmett-Teller (BET), temperature-programmed desorption of ammonia ($NH_3$-TPD), Energy-dispersive X-ray spectroscopy (EDS), and thermogravimetric analysis-differential thermal analysis (TGA-DTA). X-ray diffraction (XRD) patterns were recorded on a PANalytical X'Pert multipurpose X-ray diffractometer in the angle (2θ) range of 5° to 50° with Cu-Kα1 radiation (40 kV and 40 mA) at a rate of 2.0° $min^{-1}$. Nitrogen physisorption measurements were performed on a Micromeritics 3Flex surface characterization analyzer at −77 K. Prior to the measurements, all samples were degassed at 300° C. for 6 h. Total surface area was determined by the Brunauer-Emmett-Teller (BET) equation using the relative pressure ($P/P_0$) in the range of 0.05-0.3. External surface area was calculated using t-plot method and the pore size distribution was estimated using Barrett-Joyner-Halenda (BJH) model. Scanning electron microscopy (SEM) images were captured on a Hitachi S-4700 instrument to investigate the morphology of the materials. Energy-dispersive X-ray spectroscopy (EDS) was carried out to map the presence of various elements in the doped zeolite monoliths. Temperature-programmed desorption of ammonia ($NH_3$-TPD) was performed to investigate the acid property of the samples. $NH_3$ adsorption was carried out on the Micromeritics 3Flex analyzer under a flow of 5 vol. % $NH_3$/He at 100° C. The desorption of $NH_3$ was measured from 100 to 600° C. at a constant heating rate of 10° C. $min^{-1}$. A mass spectroscopy (BELMass) was used to detect the quantity of desorbed $NH_3$. Temperature-programmed reduction with hydrogen ($H_2$-TPR) was also performed from 50 to 850° C. under a flow of 5 vol % $H_2$/He using the same instrument. To determine the functional groups, FTIR spectra were obtained using a Nicolet-FTIR Model 750 spectrometer. Mechanical testing was also carried out to determine the mechanical integrity of the monoliths using an Instron 3369 (Instron, Norwood, Mass., USA) mechanical testing device with a 500 N load at 2.5 mm/min.

Figure 9A:
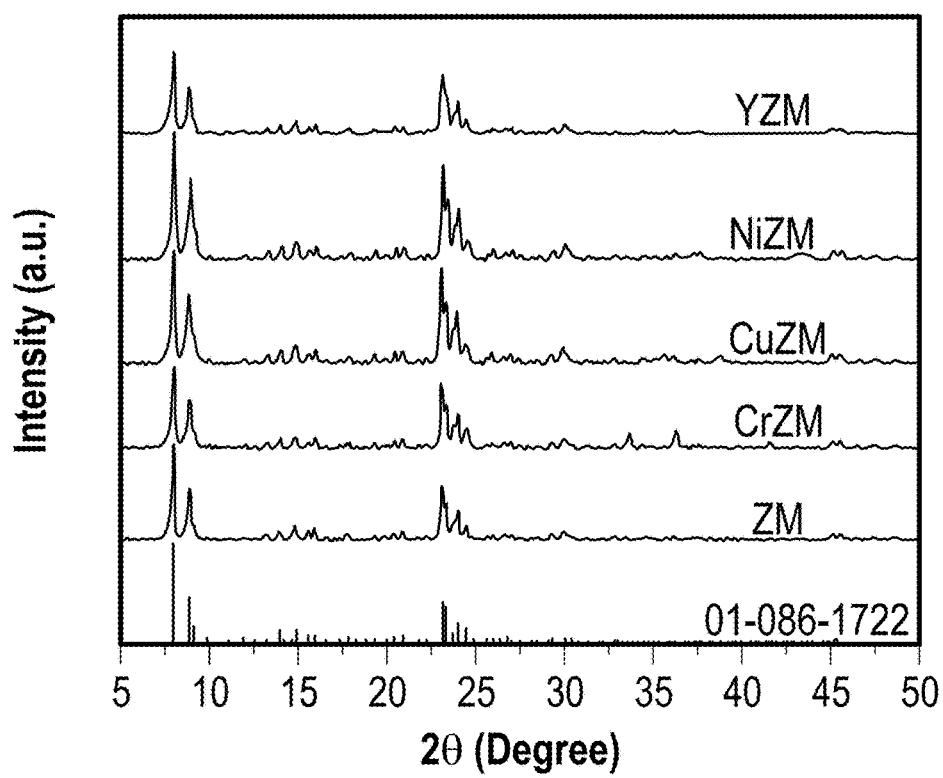
FIG. 9A depicts the XRD patterns of 3-D printed ZSM-5 monolith and metal-doped ZSM-5 zeolite monolith catalysts in the range of 2θ=5-50° as compared to the patterns of standard samples and corresponding ICDD No., according to an exemplary embodiment of the present disclosure.
Figure 9B:
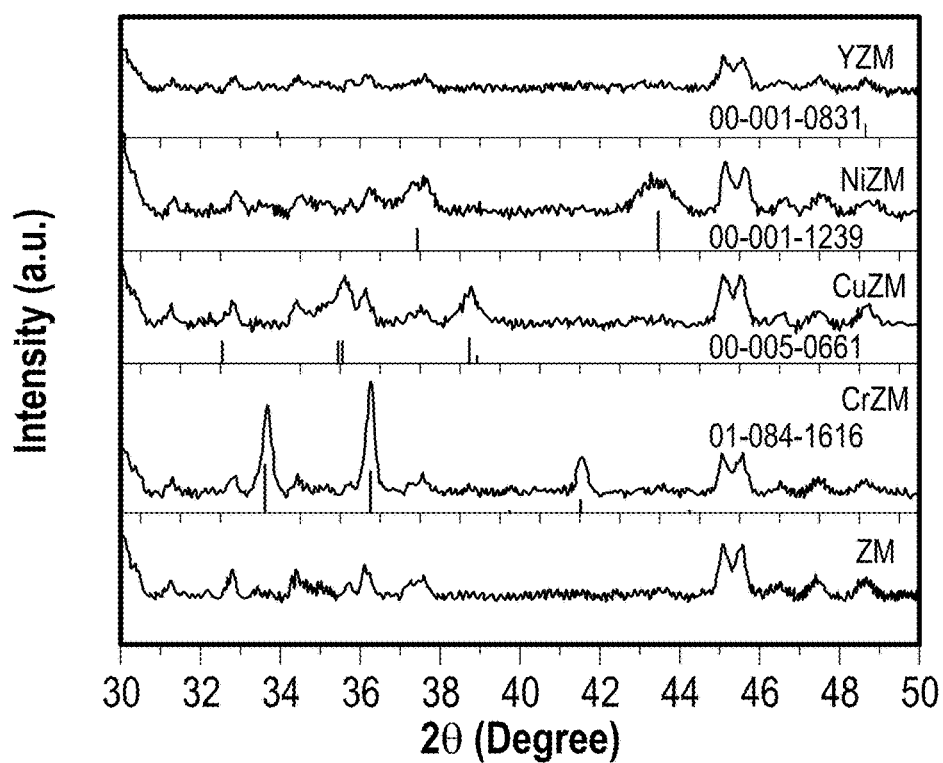
FIG. 9B depicts the XRD patterns of 3-D printed ZSM-5 monolith and metal-doped ZSM-5 zeolite monolith catalysts in the range of 2θ=30-50° as compared to the patterns of standard samples and corresponding ICDD No., according to an exemplary embodiment of the present disclosure.

The XRD patterns of the as-prepared metal-doped ZSM-5 monoliths are shown in FIGS. 9A and 9B. Comparing with the standard sample (ICDD No. 01-086-1722), characteristic peaks observed at 2θ=7.96°, 8.88°, 23.2°, 23.3° and 24.0° were attributed to (101), (200), (501), (341) and (303) planes of the zeolite crystal with MFI framework. It indicated that the framework of ZSM-5 was well retained after incorporation of metals. Scrutiny of the patterns in FIG. 9B in the range of 2θ=30-50° revealed the presence of metal oxide in three of the samples. The peaks at 2θ=33.6°, 36.1° and 41.5° in CrZM can be ascribed to (104), (110) and (113) planes in $Cr_2O_3$ (ICDD No. 01-086-1616). The weak signals found at 2θ=35.6° and 38.7° in CuZM were assigned to (002) and (111) planes of CuO, respectively (ICDD No. 00-005-0661), while the peaks at 2θ=37.2° and 43.3° in NiZM were the diffractions of (111) and (200) planes of NiO (ICDD No. 00-001-1239). The peaks suggested the formation of transition metal oxides in these three samples. As for YZM, no obvious peaks were found within the investigated angles, indicating either the absence or extremely uniform dispersion of yttrium oxide. The $H_2$-TPR profile of YZM shown later in FIG. 6 verified the latter possibility. The exact loading of the metal dopants in the 3D-printed monoliths were measured by XRF and the results are displayed in Table 3.

TABLE 3

Physical properties of the 3D-printed ZSM-5 monoliths. 286 297 317 293

| samples | $S_{BET}^a$ ($m^2 g^{-1}$) | $S_{micro}^b$ ($m^2 g^{-1}$) | $S_{ext}$ ($m^2 g^{-1}$) | $V_{total}^c$ ($cm^3 g^{-1}$) | $V_{micro}^b$ ($cm^3 g^{-1}$) | $V_{meso}$ ($cm^3 g^{-1}$) | Metal loading$^d$ (wt. %) |
|---|---|---|---|---|---|---|---|
| ZM | 373 | 214 | 159 | 0.300 | 0.100 | 0.200 | — |
| CrZM | 286 | 180 | 106 | 0.219 | 0.089 | 0.130 | 11.62 |
| CuZM | 297 | 197 | 100 | 0.202 | 0.096 | 0.106 | 9.56 |
| NiZM | 317 | 195 | 122 | 0.217 | 0.095 | 0.122 | 11.05 |
| YZM | 293 | 185 | 108 | 0.208 | 0.090 | 0.118 | 10.34 |

$^a S_{BET}$ was obtained by analyzing nitrogen adsorption data at −196° C. in a relative vapor pressure ranging from 0.05 to 0.30.
$^b$Micropore area and micropore volume were determined using t-plot method.
$^c$Total pore volume was estimated based on the volume adsorbed at $P/P_o$ = 0.99.
$^d$The metal loading was measured by XRF.

Figure 10A:
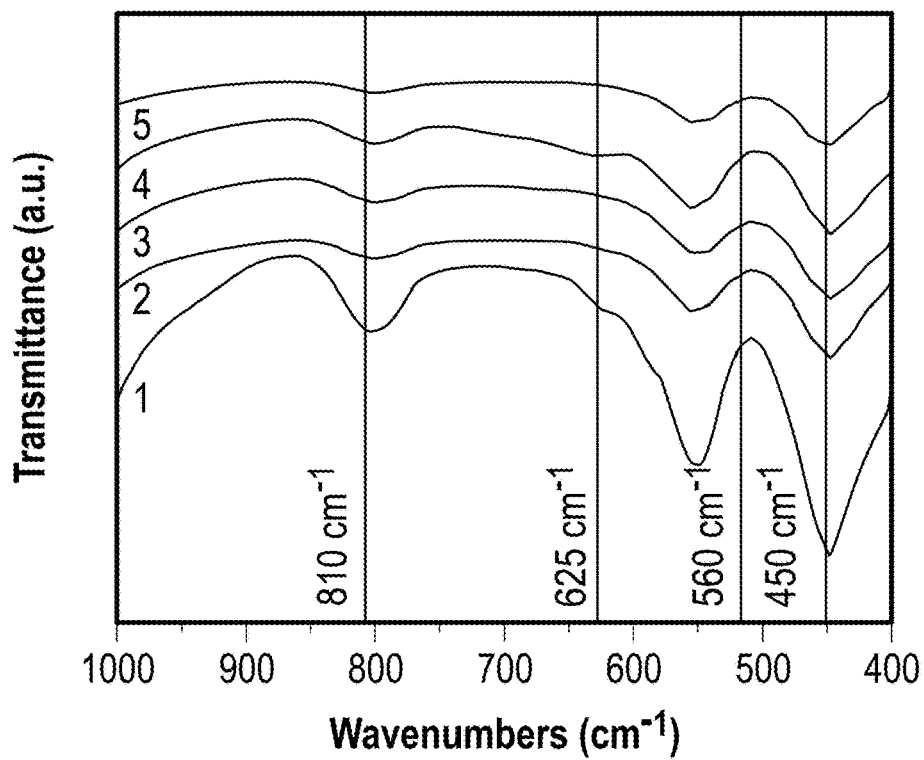
FIG. 10A depicts the FT-IR spectra of (1) ZM, (2) YZM, (3) NiZM, (4) CrZM and (5) CuZM in the range of (a) 400-1000 cm$^{-1}$, according to an exemplary embodiment of the present disclosure.
Figure 10B:
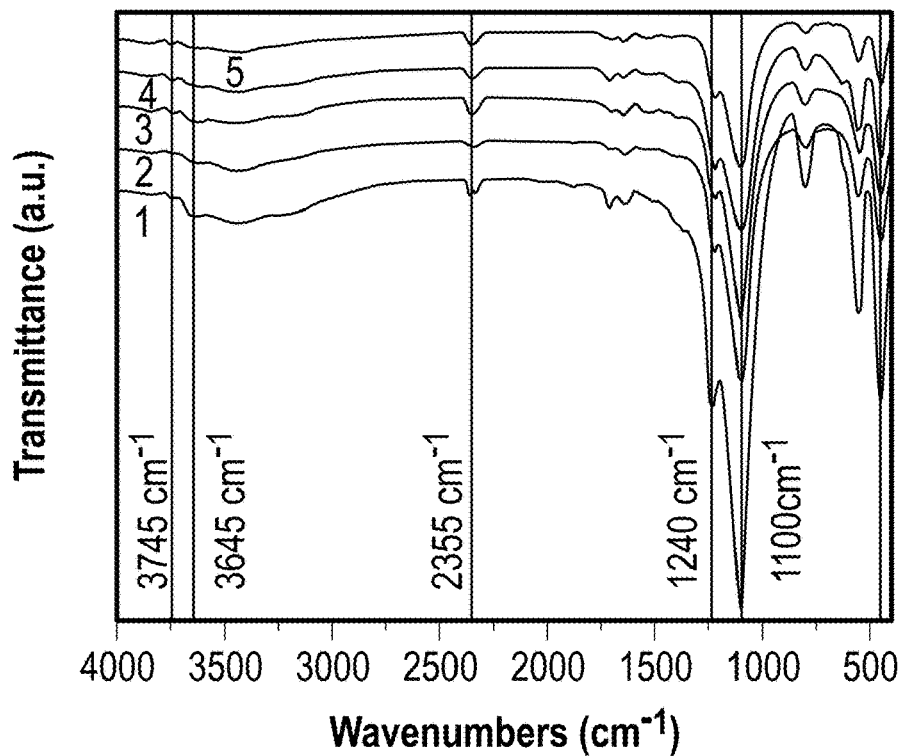
FIG. 10B depicts the FT-IR spectra of (1) ZM, (2) YZM, (3) NiZM, (4) CrZM and (5) CuZM in the range of 400-4000 cm$^{-1}$, according to an exemplary embodiment of the present disclosure.

All samples exhibited typical MFI type zeolite IR spectrum, as shown in FIGS. 10A and 10B. In detail, the peaks at about 450 $cm^{-1}$ was ascribed to the vibration of the internal T-O bonds of $TO_4$ tetrahedra The letter "T" here represents either Al or Si in the zeolite framework. The bands observed at 560 $cm^{-1}$ were generally associated with external bonds of double five-member rings. The peak appeared around 810 $cm^{-1}$ was related to symmetric stretching of external bonds between tetrahedral. The bands found at 1240 $cm^{-1}$ was a reflection of the asymmetric stretch vibration of T-O bond assigned to the external linkages between $TO_4$ tetrahedra. The most intense peak found at 1110 $cm^{-1}$ was related to the internal asymmetric stretching of Si—O-T bonds. In the hydroxyl group region at higher wavenumbers, the peak at 3745 $cm^{-1}$ was ascribed to the —OH vibration of the silanol groups (Si—OH), mostly on the external surface of the zeolite. The peak around 3645 $cm^{-1}$ was regarded as the reflection of Al—OH groups. The peak observed at 625 cm$^{-1}$ in CrZM corresponded to the stretching vibration of Cr—O bond. Other samples showed no obvious peaks of the oxide due to the small particle sizes of formed CuO, NiO and $Y_2O_3$.

Figure 11A:
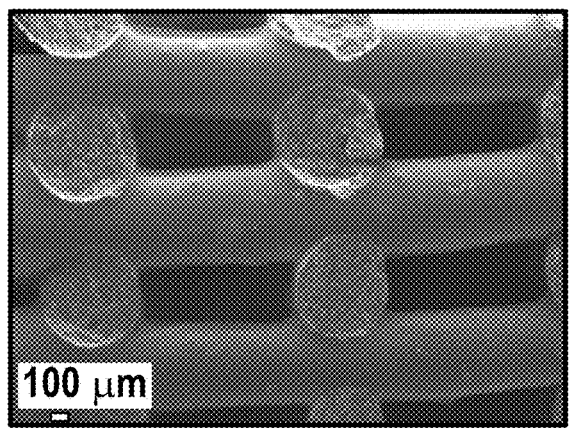
FIG. 11A depicts a SEM micrograph of the side view of ZM internal channels, according to an exemplary embodiment of the present disclosure.
Figure 11B:
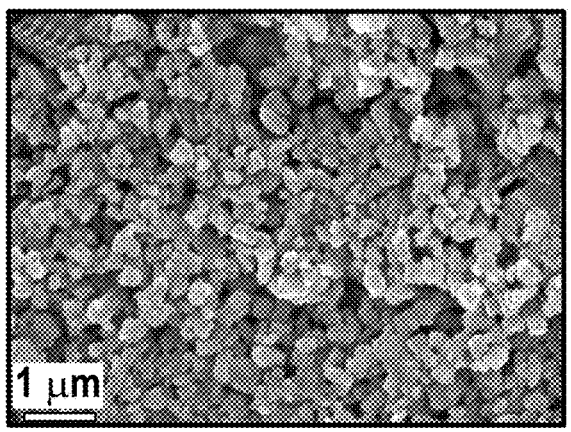
FIG. 11B depicts a SEM micrograph of the surface of ZM, according to an exemplary embodiment of the present disclosure.
Figure 11C:
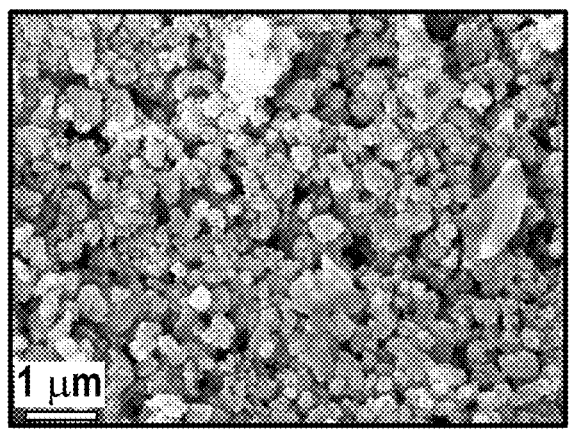
FIG. 11C depicts a SEM micrograph of CrZM, according to an exemplary embodiment of the present disclosure.
Figure 11D:
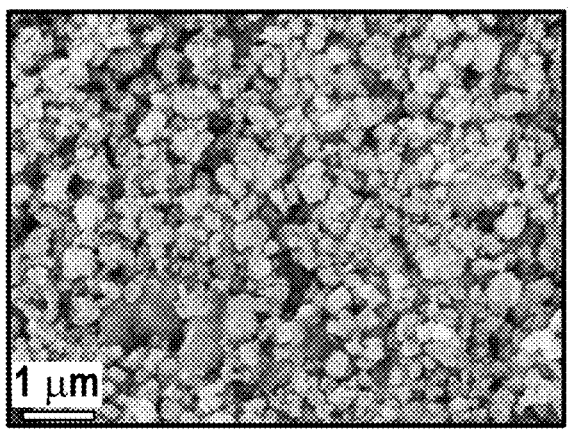
FIG. 11D depicts a SEM micrograph of CuZM, according to an exemplary embodiment of the present disclosure.
Figure 11E:
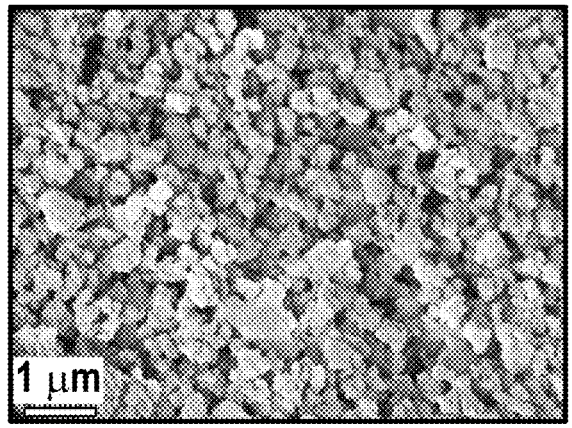
FIG. 11E depicts a SEM micrograph of NiZM, according to an exemplary embodiment of the present disclosure.
Figure 11F:
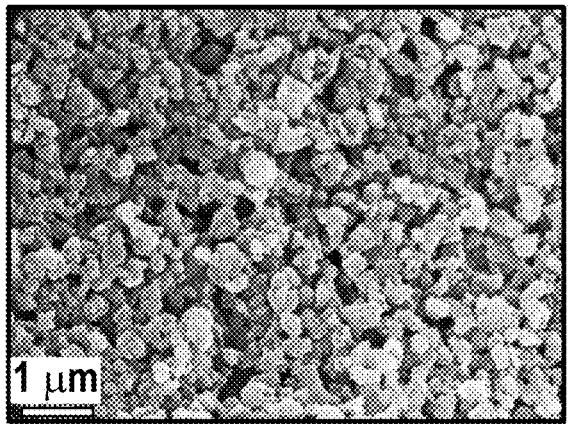
FIG. 11F depicts a SEM micrograph of YZM, according to an exemplary embodiment of the present disclosure.
Figure 12A:
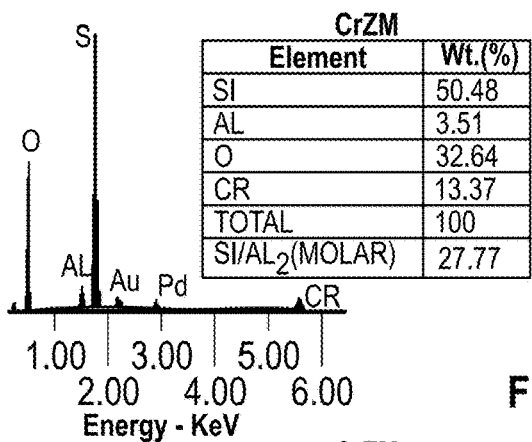
FIG. 12A depicts the EDS mapping analysis of CrZM, according to an exemplary embodiment of the present disclosure.
Figure 12A:
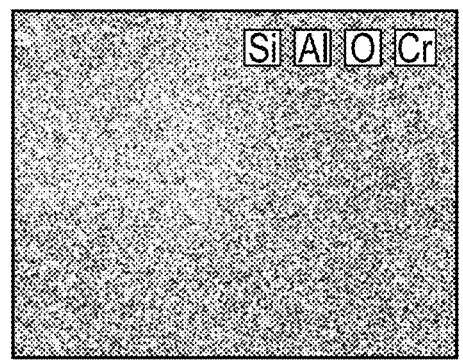
Figure 12B:
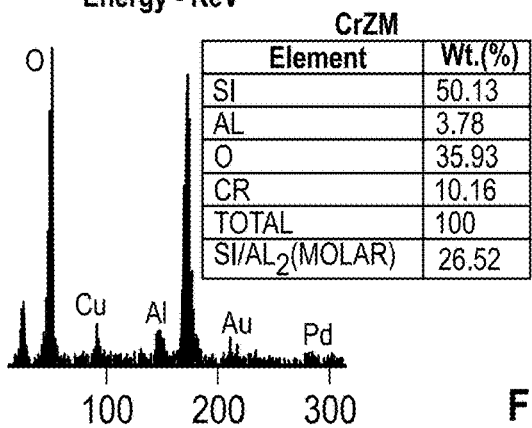
FIG. 12B depicts the EDS mapping analysis of CuZM, according to an exemplary embodiment of the present disclosure.
Figure 12B:
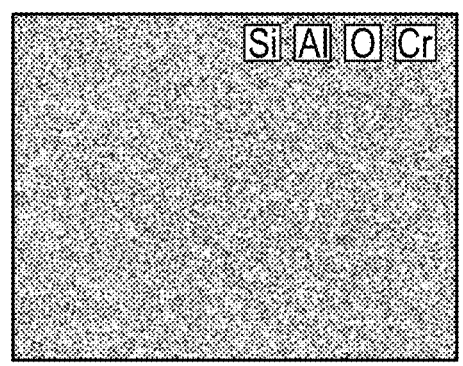
Figure 12C:
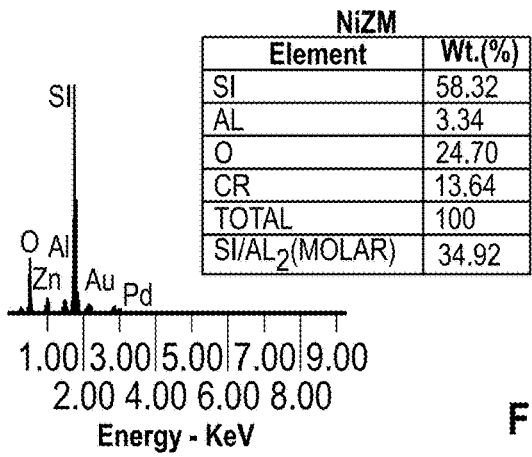
FIG. 12C depicts the EDS mapping analysis of NiZM, according to an exemplary embodiment of the present disclosure.
Figure 12C:
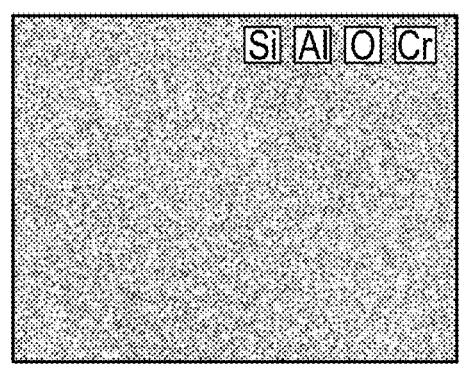
Figure 12D:
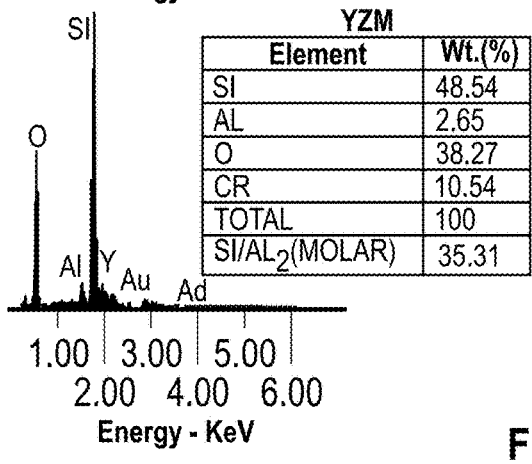
FIG. 12D depicts the EDS mapping analysis of YZM, according to an exemplary embodiment of the present disclosure.
Figure 12D:
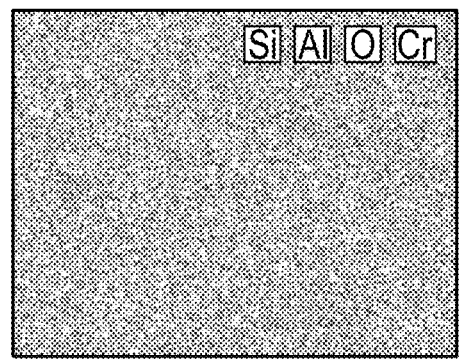

FIG. 11A shows the micrograph of the side view of the 3D-printed ZSM-5 monolith channels. These interconnected channels created by the layer-by-layer deposition via the 3D printer provided more contact between the fluid and the catalysts active sites, compared to traditional independent channels. The surface morphology of the zeolite monolith is displayed in FIGS. 11B-F. It is evident from these micrographs that the zeolite particles adhered to each other due to the addition of binder, which made the monolith a self-standing configuration. Pores of a broad range of size distribution, generated from the removal of methyl cellulose, can be observed on the monolith surface. In addition, the surface morphology, of the bare zeolite monolith and metal-modified zeolite monoliths were found to be similar in terms of particle size and pore geometry. Notably, CuZM and NiZM exhibited rougher particle surfaces than the other samples, which might be the result of the formation of metal oxide which changed the particle surface morphology. The difference in the appearance of the doped-zeolite monoliths could be correlated to the difference in the particle size and surface texture of the metal oxides. FIG. 12 show the EDS analysis of the metal doped samples, i.e., CrZM (FIG. 11A), CuZM (FIG. 11B), NiZM (FIG. 11C) and YZM (FIG. 11D). All samples exhibited well-dispersed metal on the monolith surface and the actual metal loading is accordance with the expected value.

Figure 13:
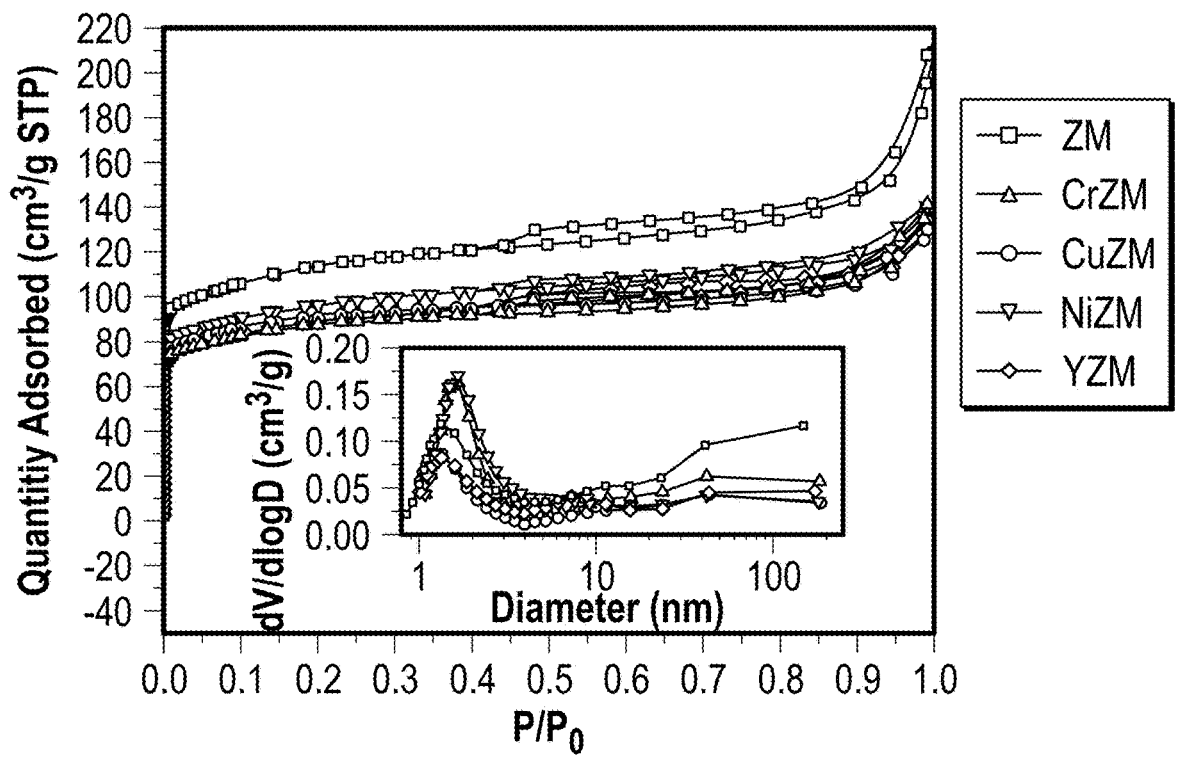
FIG. 13 depicts nitrogen adsorption-desorption isotherms at −196° C. and BJH pore size distribution (inset), according to an exemplary embodiment of the present disclosure.

The $N_2$ adsorption-desorption isotherms and their corresponding pore size distribution of the studied materials are presented in FIG. 13. Overall, the ZM monolith displayed higher $N_2$ uptake than the other metal-modified zeolite monoliths. All samples exhibited Type IV isotherms with hysteresis loops of various sizes in relative pressure range of 0.45 to 1.0. The textural properties of all 3D-printed monoliths are shown in Table 3. The BET surface area decreased from 373 m$^2$/g to 286, 297, 317, 293 m$^2$/g for, CrZM, CuZM, NiZM and YZM, respectively. The lower surface area of the metal-modified zeolite monolith was due to the formation of metal oxide during doping. Similarly, the pore volume also reduced from 0.300 cm$^3$ g$^{-1}$ to 0.219, 0.202, 0.217 and 0.208 cm$^3$ g$^{-1}$ for CrZM, CuZM, NiZM and YZM, respectively. It should be noted here that the slight change in microporous volume, calculated from t-plot method, indicated that the decrease in the total pore volume was mainly originated from the reduction in the mesopore volume. The inset of FIG. 13 shows the distribution of the pore sizes. The multiple peaks observed for all samples, in addition to the intrinsic monolith channels, suggested the 3D-printed monoliths possess a hierarchical macro-meso-microporous network. The decrease in the pore volume was the result of the dramatic volume decline of the mesopores ranging from 10 to 50 nm. The effect of metal modification on the size of the pores in the 1-5 nm range was different for different metals. While CuZM and YZM displayed lower peaks in this range, CrZM and NiZM gave rise to higher peak intensities, as a result of the formed chromium oxide and nickel oxide, which had dominant mesopores in this range.

Figure 14:
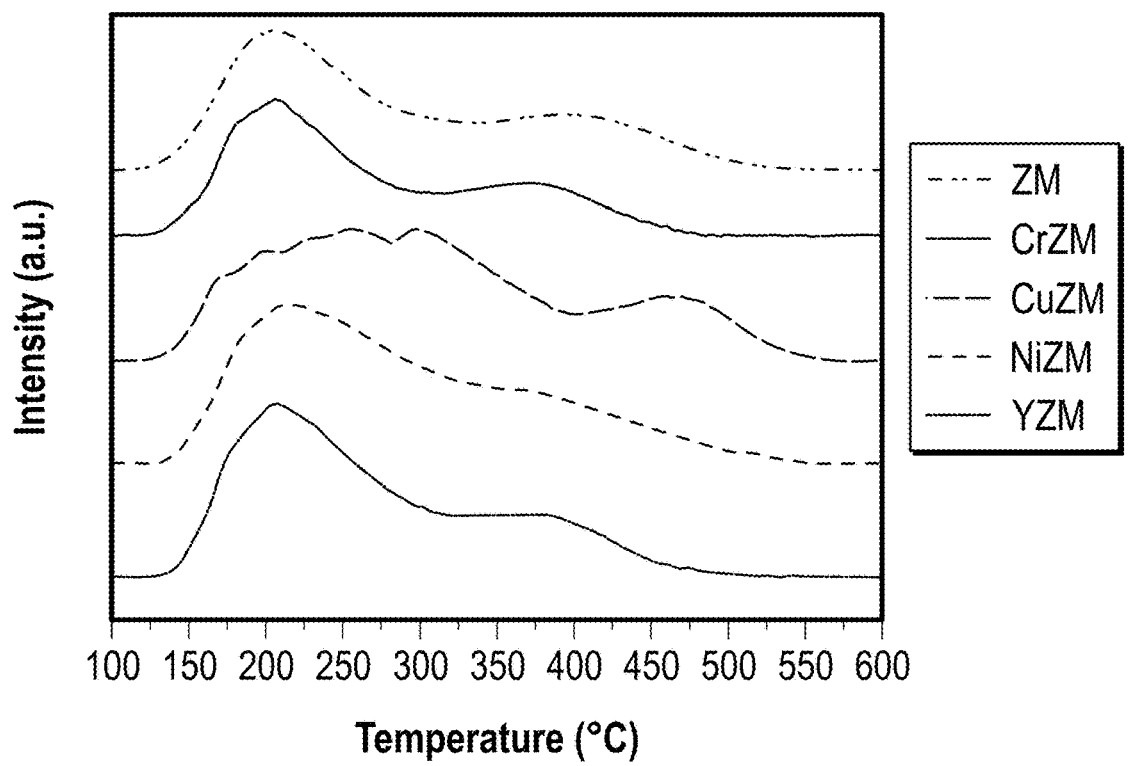
FIG. 14 depicts NH$_3$-TPD profiles for the 3D-printed ZSM-5 monolith and metal doped ZSM-5 monoliths, according to an exemplary embodiment of the present disclosure.

FIG. 14 summarizes the acidic properties of the 3D-printed zeolite monoliths determined from $NH_3$-TPD profiles with corresponding strong and weak acid sites amounts listed in Table 4. The intensity refers to the amount of $NH_3$ desorbed from the samples pretreated with $NH_3$ chemical adsorption. For bare ZSM-5 monolith, two peaks at 207° C. and 394° C. represented the weak and the strong acid sites on the surface, respectively. The area under each peak is proportional to the number of acid sites. Both CrZM and YZM samples showed increased amount of weak acid sites with similar peak around 205° C., however the strong acid sites peaks shifted to lower temperatures of 371 and 385° C., respectively, indicating the strength of the acid sites was moderated by the metal modification in these two samples. For CrZM and YZM, the smaller peak area for strong acid sites suggested the reduced number of strong acid sites, whereas NiZM exhibited increased number of weak acid sites. The effect of Cu on the acid site was complex according to the unique pattern of the TPD profile. CuZM displayed a broad peak in the range of 150 to 400° C. and another peak from 400 to 600° C., indicating the strength of the strong acid sites increased after modified with Cu, consistent with previous work.

TABLE 4

Summary of TPD and TPR results.

| | Weak acid peak[a] | | Strong acid peak[a] | | Total | $H_2$ Reduction | | TPR Peak Area[b] |
|---|---|---|---|---|---|---|---|---|
| | | Amount | | Amount | amount[a] | Peak[b] | | (a.u.) × |
| Sample | T (K) | (mmol g$^{-1}$) | T (K) | (mmol g$^{-1}$) | (mmol g$^{-1}$) | No. | T (K) | 10$^{-8}$ |
| ZM | 207 | 0.40 | 394 | 0.16 | 0.56 | — | — | — |
| CrZM | 205 | 0.31 | 371 | 0.13 | 0.44 | a | 285 | 4.55 |
| CuZM | 297 | 0.56 | 459 | 0.15 | 0.72 | a | 206 | 5.67 |
| | | | | | | b | 625 | 4.25 |
| NiZM | 216 | 0.55 | 376 | 0.13 | 0.68 | a | 209 | 4.48 |
| | | | | | | b | 366 | 2.38 |
| YZM | 208 | 0.52 | 385 | 0.07 | 0.59 | a | 331 | 2.72 |
| | | | | | | b | 686 | 2.68 |

[a]obtained from $NH_3$-TPD results
[b]obtained from $H_2$-TPR results

Figure 15:
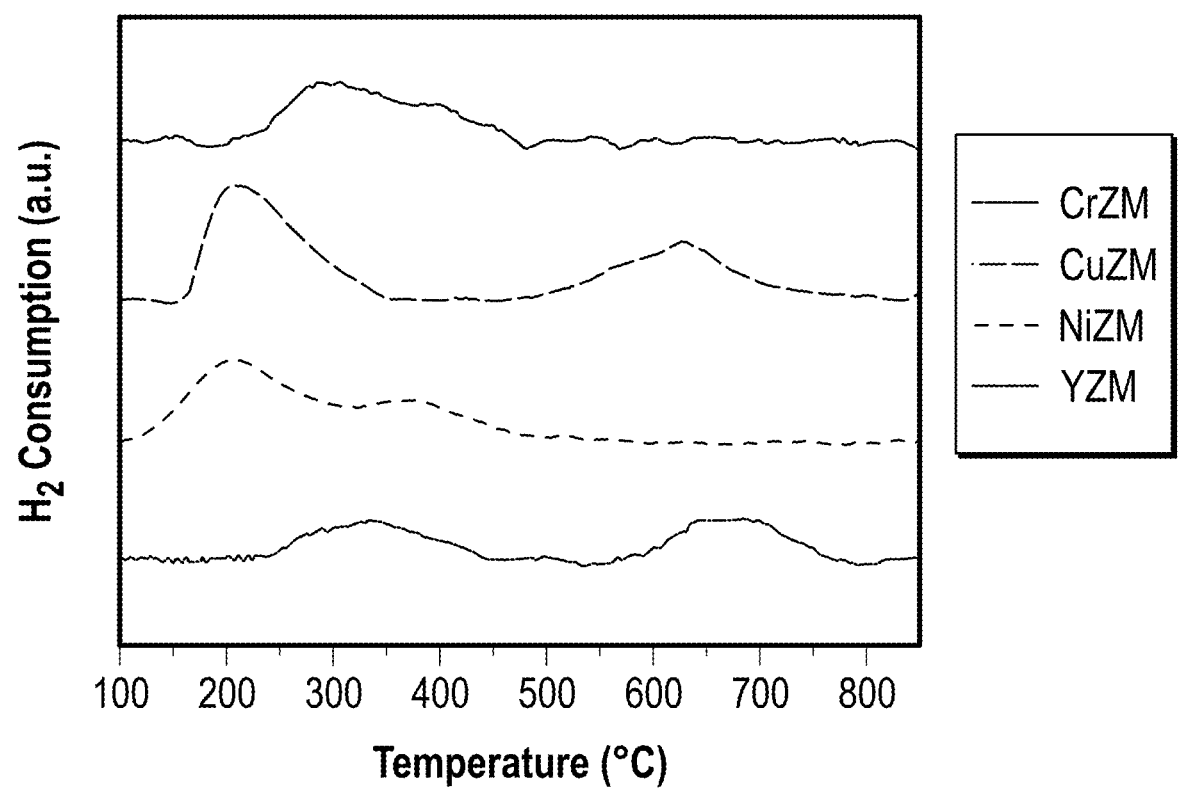
FIG. 15 depicts H$_2$-TPR profiles of the 3D-printed metal doped ZSM-5 monoliths, according to an exemplary embodiment of the present disclosure.

The $H_2$-TPR results for all metal-modified monoliths are presented in FIG. 15 and the peaks position with corresponding areas are shown in Table 4. For CrZM, the peak appeared at around 285° C. was due to the reduction of Cr$^{3+}$ to Cr$^0$, consistent with results of previous studies. The result was consistent with the XRD pattern showing the formation of $Cr_2O_3$. CuZM had peaks centered at 220 and 640° C., respectably. The former peak can be attributed to the reduction of bulk CuO, whereas the latter peak can be can be assigned to the replacement of Cu$^{2+}$ cation with H$^+$ in the zeolite hydroxyl groups, which needs a higher temperature to be reduced than CuO. The peaks observed in YZM profile at 331 and 686° C. were ascribed to small $Y_2O_3$ particles and yttrium cation exchanged on zeolite. The peak at around 240° C. was attributed to the reduction of NiO with small particles, whereas the peak centered at 400° C. was assigned to the bulk NiO, as was reflected in XRD patterns.

Example 7

Catalyst Evaluation of the 3D-Printed Metal-Doped Porous ZSM-5 Zeolite Monolith Catalysts The metal-modified 3D-printed ZSM-5 monoliths and their bare counterpart prepared according to Example 5 were tested in the catalytic cracking of n-hexane at 600and 650° C. Alkane catalytic cracking over zeolites is typically performed in this temperature range. Catalyst tests were carried out in a stainless steel packed-bed reactor with an internal diameter of 10 mm and a length of 300 mm. The reactant n-hexane was fed to the system from a saturator by controlling nitrogen flow rate at 30° C. A mass flow controller (Brooks, 5850) was used to control the feed flow rate. About 0.3 g of each catalyst was tested under 600 and 650° C. at 1.01 bar. A constant weight hourly space velocity (WHSV) of 5 $h^{-1}$ was used. Prior to the reaction, the catalyst was activated in-situ at 500° C. in nitrogen flow for 2 h. The reaction products were analyzed on-line every 1 h with a gas chromatography (SRI 8610C) equipped with a flame ionized detector (GC-FID) connected to mxt-wax/mxt-alumina capillary column for hydrocarbons. The effluent line of the reactor until GC injector was kept at 110° C. to avoid potential condensation of the hydrocarbons.

Figure 16A:
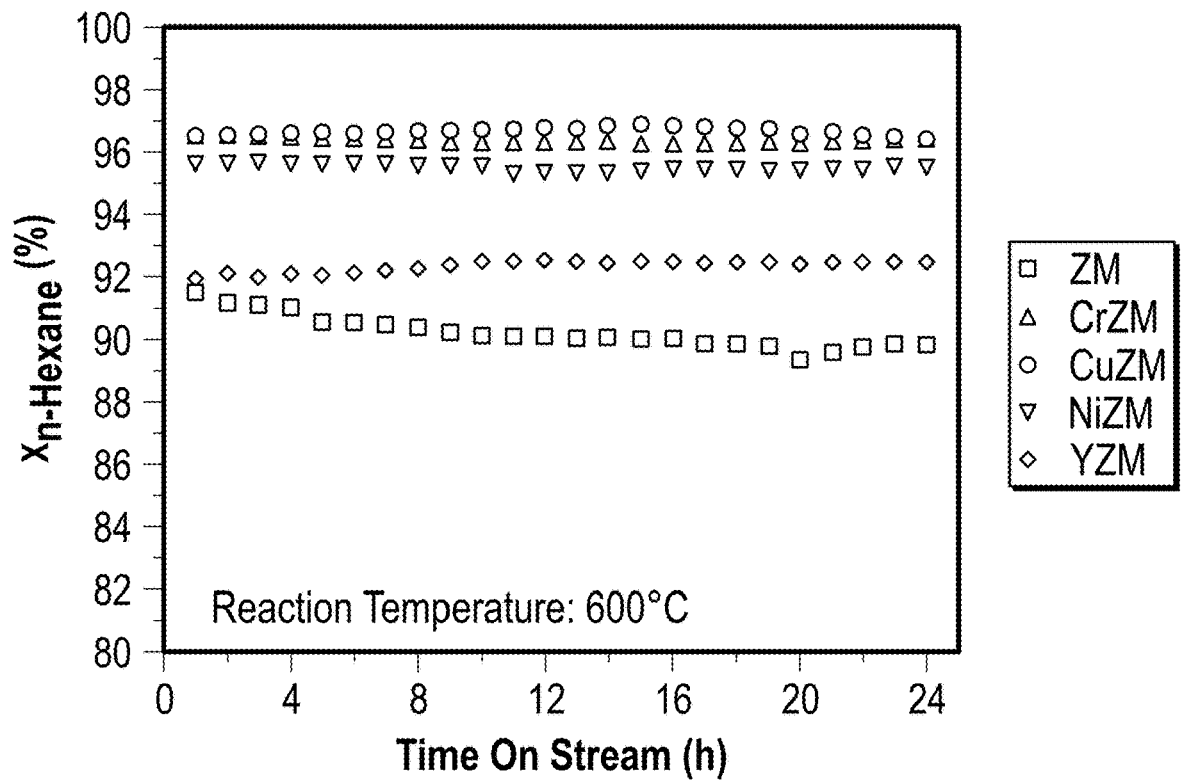
FIG. 16A depicts the conversion of n-hexane as a function of time on stream for the 3D-printed ZSM-5 monolith and metal-doped ZSM-5 zeolite monolith catalysts at 600° C., where the reactant is n-hexane, WHSV is 5 h$^{-1}$, the time on stream is 24 h, and the pressure is 1.01 bar, according to an exemplary embodiment of the present disclosure.

The conversion curves of n-hexane ($X_{n-hexane}$) as a function of time-on-stream over monolith are displayed in FIG. 16. At 600° C., all MeZM samples exhibited higher conversion than the bare ZSM-5 monoliths, as shown in FIG. 16A. Moreover, it can be seen that the metal modification made the catalysts more stable in the n-hexane cracking process at 600° C. Although the decrease in $X_{n-hexane}$ from 91.5% in 1 h to 90% in 24 h was marginal, the modified samples maintained nearly constant throughout at the investigated times. Among the metal modified samples, CuZM exhibited the highest n-hexane conversion of 97%, which could be attributed to the high amount of acid sites, enhanced acid sites strength and the generated reduced sites on the monolith surface, as discussed in TPD and TPR results. Other modified ZSM-5 monoliths also showed improved activity. It was also found that the conversion of n-hexane at 650° C. was higher than that at 600° C. over all the investigated monoliths in the initial stage of the reaction. ZM, CrZM, CuZM, and NiZM experienced a gradual conversion decline suggesting the formation of coke deposition and, hence, deactivation of the catalysts. Considering the long period of reaction time of 24 h, the decrease within 5% was minor and non-severe. As discussed in previous paper, the good stability stemmed from the creation of the monoliths with hierarchical porosity which favored the mass transfer of the intermediates and products, which further suppressed secondary reactions such as aromatic polymerization and reduced coke formation.

Figure 16B:
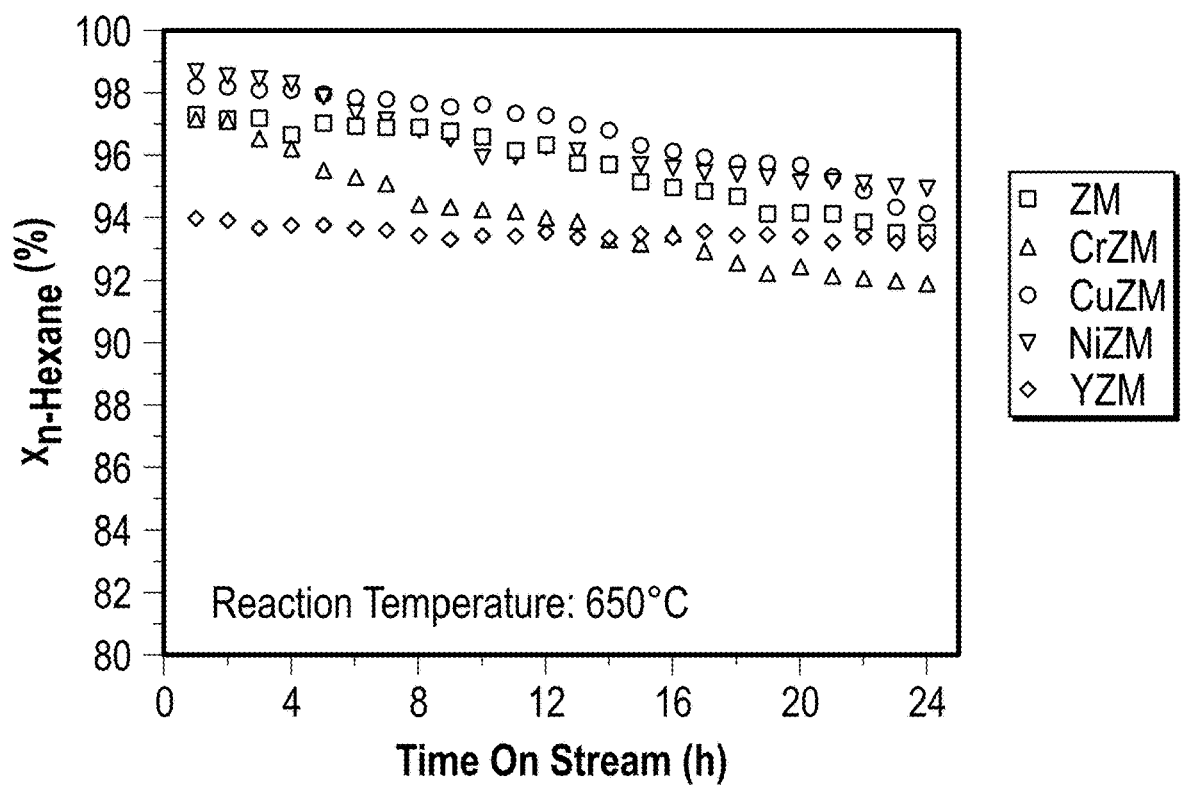
FIG. 16B depicts the conversion of n-hexane as a function of time on stream for the 3D-printed ZSM-5 monolith and metal-doped ZSM-5 zeolite monolith catalysts at 650° C., where the reactant is n-hexane, WHSV is 5 h$^{-1}$, the time on stream is 24 h, and the pressure is 1.01 bar, according to an exemplary embodiment of the present disclosure.

Investigating the compounds detected in the product stream of the n-hexane cracking reaction, it was found that the main products consisted of olefins ($C_2=-C_5=$), paraffin ($C_1-C_5$) and BTX. FIGS. 16A and 16B depict a summary of the selectivity towards the aforementioned hydrocarbons in three stages of the reaction: 1 h on stream, the initial stage of the reaction; 10 h on stream, the medial stage of the reaction; and 24 h on stream, the final stage of the reaction. In these two figures, ethylene, propylene, and butylene are stacked in one column since they are all categorized as light olefins. The other products, i.e. BTX, paraffin and other hydrocarbons, are listed in individual columns. In each stage of the reaction, the catalysts are displayed and compared in the following order: bare ZSM-5 and ZSM-5 monoliths modified with Cr, Cu, Ni, and Y.

Figure 17A:
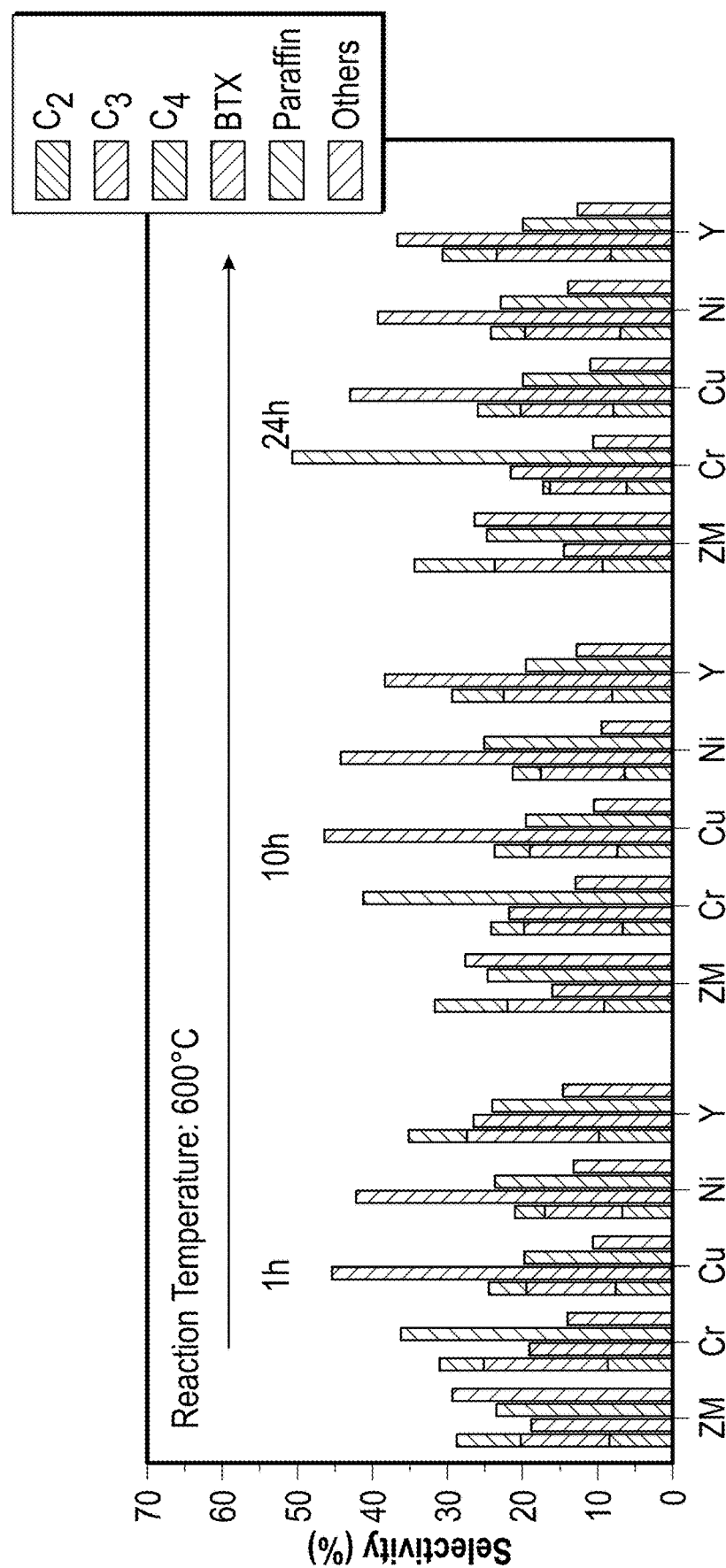
FIG. 17A depicts product distribution for the 3D-printed ZSM-5 monolith and metal-doped ZSM-5 zeolite monolith catalysts at 600° C., where the reactant is n-hexane, WHSV is 5 h$^{-1}$, the time on stream is 24 h, and the pressure is 1.01 bar, according to an exemplary embodiment of the present disclosure.

As evident from FIG. 17A, CrZM and YZM exhibited a higher selectivity towards light olefins than ZM in the initial stage of the reaction at 600° C. With the reaction evolution, the CrZM and YZM experienced a gradual decrease in light olefin selectivity, whereas the selectivity variation over CuZM and NiZM was insignificant indicating that all MeZM samples produced less light olefins than their bare counterpart in the medial and final stage of the reaction. Among the investigated catalysts, CuZM, NiZM and YZM showed outstanding performance in producing BTX. The formation of BTX might be the results of the aromatization of paraffin with shorter carbon numbers (e.g. ethane and butane), which was produced during the β-scission of the carbenium ion, according to the Haag-Dessau cracking mechanism. The modification with Cu and Ni promoted the aromatization process under the reaction conditions investigated and hence increased the selectivity towards BTX, in accordance with previously reported works. The effect of yttrium modification of MFI zeolite on catalytic cracking in existing literature is scarce. Our catalytic results showed that the YZM promoted the production of BTX by reducing the paraffin selectivity at 600° C. in the later stage of the reaction.

Figure 17B:
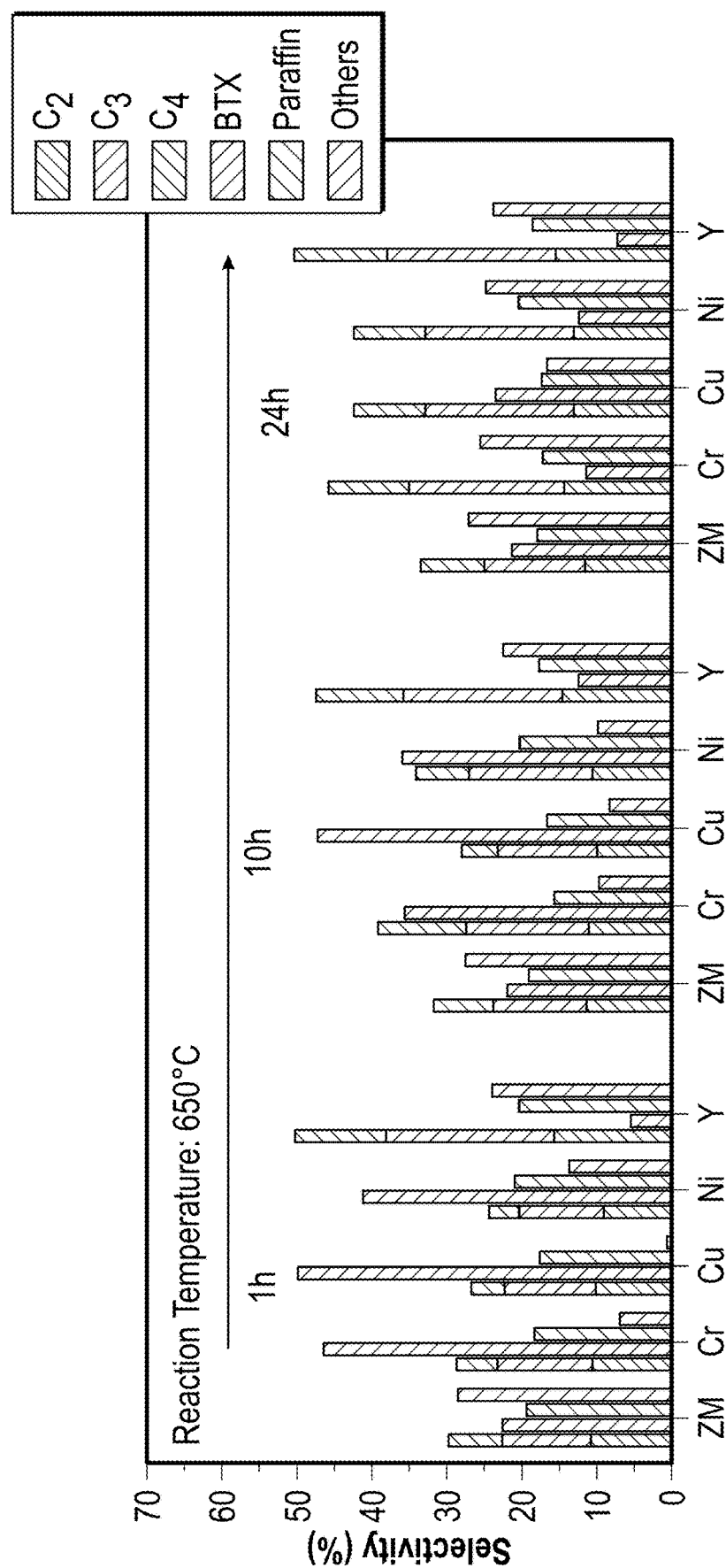
FIG. 17B depicts product distribution for the 3D-printed ZSM-5 monolith and metal-doped ZSM-5 zeolite monolith catalysts at 650° C., where the reactant is n-hexane, WHSV is 5 h$^{-1}$, the time on stream is 24 h, and the pressure is 1.01 bar, according to an exemplary embodiment of the present disclosure.

The products distribution at 650° C. is displayed in FIG. 17B. At this temperature, Cu and Ni-modified monoliths retained their outstanding selectivity towards BTX in 1 and 10 h on stream. In addition, CrZM exhibited an enhanced production of BTX in these reaction stages. However, YZM experienced a significant decrease in BTX selectivity when the temperature was increased to 650° C. All the catalysts displayed a higher light olefins selectivity than at 600° C., suggesting that the increased temperature not only enhanced the activity but also favored the production of light olefins. With the evolution of the reaction, ZM, CrZM, CuZM, and NiZM experienced an increasing trend for selectivity towards light olefins, whereas YZM displayed a steady behavior. Dupain et al. described that the initial stages of the FCC process involves mostly thermal (radical) cracking on the outer surface, especially at high temperature. The generated paraffin are catalyzed by metal sites and are promoted to produce aromatics. In the developed stages of the reaction, the process involves catalytic conversion on Brønsted acid sites, which dispersed in the internal cages of the MFI frameworks in the zeolite and acted as the active sites to donate proton in hydrogen transfer step and produce carbonium ions which are the precursor of the light olefins.

Figure 18:
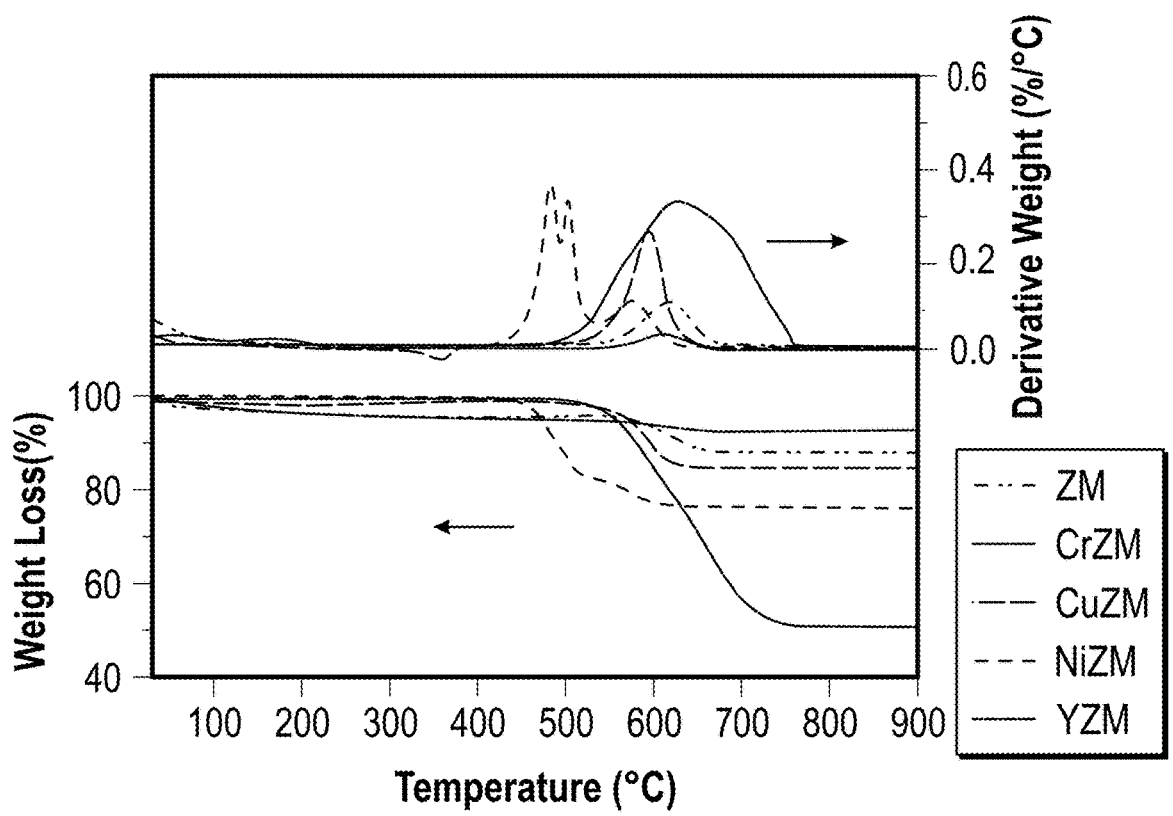
FIG. 18 depicts TGA (lower) and DTA (upper) profiles of the spent catalysts after n-hexane cracking at 650° C. for 24 h for the 3D-printed ZSM-5 monolith and metal-doped ZSM-5 zeolite monolith catalysts, according to an exemplary embodiment of the present disclosure.

Since each catalyst exhibited a certain degree of deactivation at 650° C., TGA of the spent catalysts after 24 h of n-hexane cracking was carried out in the temperature range of 30-900° C. The TGA and DTA profiles are depicted in FIG. 18. For NiZM, two peaks in the range of 420-540° C. were observed which were assigned to the soft coke associated with the condensation and subsequent growth of coke precursors in the catalyst pore system. This result indicated that the Ni dopant prevented the coke precursor from growing further into heavier cokes. All other monoliths showed a dramatic weight loss after 550° C. CrZM not only showed the highest weight loss, indicative of most severe deactivation in agreement with conversion trend, but also exhibited a broad DTA peak, indicative of the formation of various types of coke with various molecular weights. The yttrium was the only dopant that enhanced the coke resistance nature of the catalyst, according to its reduced amount of coke in comparison with bare ZSM-5 monoliths. This coke resistance behavior could be attributed to the relatively low conversion of n-hexane over YZM, moderated acidity, and small amount of reduction sites.

Figure 19:
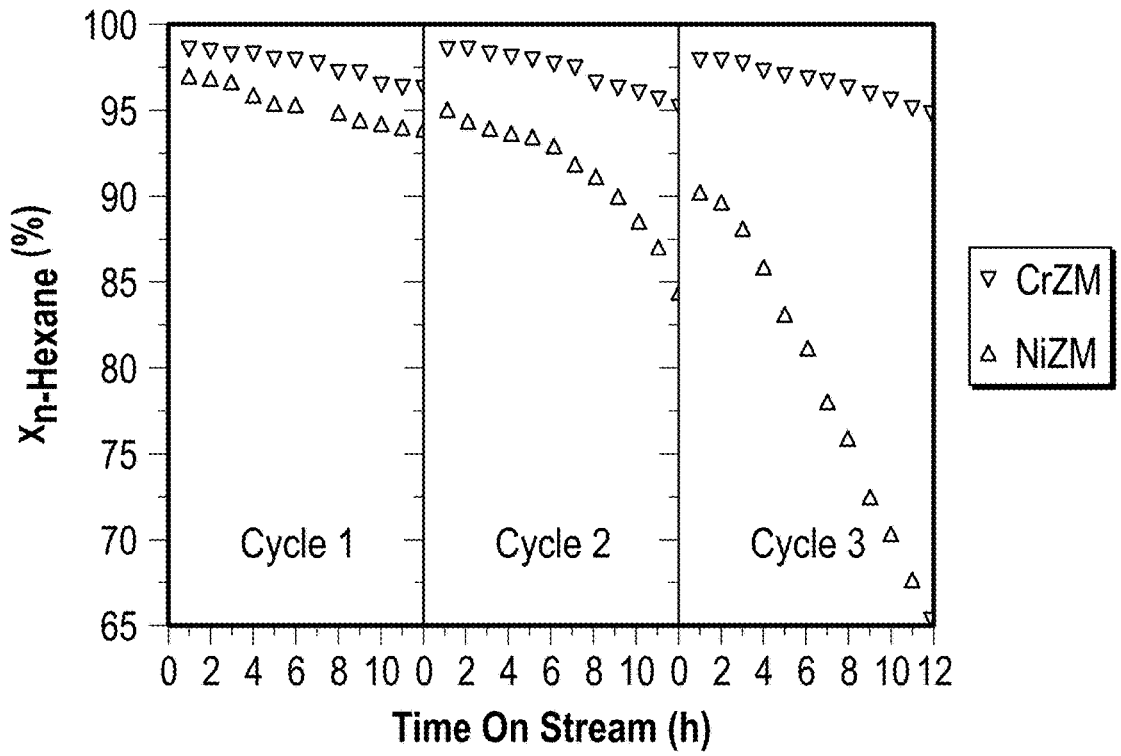
FIG. 19 depicts the activity of the CrZM and NiZM metal-doped zeolite monolith catalysts as a function of time-on-stream in three cycles, where the reaction conditions are 650° C., WHSV is 5 h$^{-1}$, and the regeneration condition is 700° C. for 4 h with air flow according to an exemplary embodiment of the present disclosure.

To study the recyclability of the metal-doped 3D-printed ZSM-5 monoliths in n-hexane cracking reaction, CrZM and NiZM monoliths were calcined at 700° C. for 4 h in air to remove the coke from and regenerate the spent catalysts after 12 h of time-on-stream. These two samples were selected for the recyclability tests because they both exhibited a relatively high coke formation and there was an essential difference between their coke types, as evident in the DTA peak positions (see FIG. 18). Both catalysts were regenerated twice and tested again under the same conditions as fresh catalysts. The activity as a function of time-on-stream in each cycle is depicted in FIG. 19. It can be noted that the recyclability of CrZM was poor due to the large amount and high molecular weight of the formed coke. The DTA profile of CrZM monolith suggested that the total coke removal can be achieved at temperatures above 760° C. However, it has been shown that higher temperature would cause significant reduction in zeolite crystallinity and substantial decrease in pore volumes. The regeneration temperature of 760° C. in this study was not clearly adequate to remove all the coke formed during reaction. Remaining coke in the zeolite accelerated the coke formation in the later cycles of the reaction, leading to a more rapid deactivation of the catalyst. On the other hand, NiZM monolith exhibited a good performance after regeneration. The n-hexane conversions over this catalyst were 98.7%, 98.7%, and 98.0% in three cycles, respectively, indicating the Ni-doped 3D-printed monolith could be regenerated for n-hexane cracking. These results correlate well with the DTA peaks of NiZM shown in FIG. 9, which revealed that the coke could be removed under 650° C.

STATEMENTS OF THE PRESENT DISCLOSURE

Numerous examples are provided herein to enhance understanding of the present disclosure. A specific set of statements are provided as follows.

Statement 1: A composition for the catalytic cracking of alkanes, the composition comprising: a porous zeolite monolith.

Statement 2: A composition according to Statement 1, wherein the porous zeolite monolith is prepared layer by layer using a 3D printer.

Statement 3: A composition according to Statement 1 or Statement 2, wherein the porous zeolite monolith is a 3D-printed porous zeolite monolith.

Statement 4: A composition according to any one of the preceding Statements 1-3, wherein the porous zeolite monolith comprises interconnected channels.

Statement 5: A composition according to Statement 4, wherein the interconnected channels are formed by layer-by-layer deposition using a 3D printer.

Statement 6: A composition according to any one of the preceding Statements 1-5, wherein the porous zeolite monolith comprises macro-meso-microporosity.

Statement 7: A composition according to any one of the preceding Statements 1-5, wherein the porous zeolite monolith is characterized by macro-meso-microporosity.

Statement 8: A composition according to any one of the preceding Statements 1-7, wherein the porous zeolite monolith comprises a plurality of micropores and a plurality of mesopores, the micropores having a diameter of greater than 15 nanometers and the mesopores having a diameter of from 2 nanometers to 15 nanometers.

Statement 9: A composition according to any one of the preceding Statements 1-8, wherein the porous zeolite monolith is selected from the group consisting of a ZSM-5 zeolite monolith, a HZSM-5 zeolite monolith, and a HY zeolite monolith.

Statement 10: A composition according to any one of the preceding Statements 1-8, wherein the porous zeolite monolith is a 3D-printed ZSM-5 zeolite monolith comprising a MFI framework.

Statement 11: A composition according to any one of the preceding Statements 1-8, wherein the porous zeolite monolith is a 3D-printed HZSM-5 zeolite monolith comprising a MFI framework.

Statement 12: A composition according to any one of the preceding Statements 1-8, wherein the porous zeolite monolith is a 3D-printed HY zeolite monolith comprising a FAU framework.

Statement 13: A composition according to any one of the preceding Statements 1-12, further comprising a silicoaluminophosphate with chabazite (SAPO-34) framework coated onto the porous zeolite monolith.

Statement 14: A composition according to any one of the preceding Statements 1-12, wherein the porous zeolite monolith further comprises a coating, the coating comprising a silicoaluminophosphate with chabazite (SAPO-34) framework.

Statement 15: A composition according to Statement 13 or Statement 14, wherein the SAPO-34 framework comprises a coating on the porous zeolite monolith formed by a secondary growth method.

Statement 16: A composition according to any one of the preceding Statements 1-15, wherein the porous zeolite monolith is a metal-doped porous zeolite monolith comprising a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof.

Statement 17: A composition according to Statement 16, wherein the metal-doped porous zeolite monolith is formed from a zeolite paste doped with a metal precursor.

Statement 18: A composition according to Statement 17, wherein the metal precursor is a metal nitrate compound.

Statement 19: A composition according to Statement 17, wherein the metal precursor is selected from the group consisting of $Cr(NO_3)_3.9H_2O$, $Cu(NO_3)_2.2.5H_2O$, $Ni(NO_3)_2.6H_2O$, and $Y(NO_3)_3.6H_2O$.

Statement 20: A composition according to any one of the preceding Statements 16-19, wherein the metal-doped porous zeolite monolith comprises from about 1 wt % to about 20 wt % metal content.

Statement 21: A composition according to any one of the preceding Statements 16-19, wherein the metal-doped porous zeolite monolith comprises from about 2.5 wt % to about 12 wt % metal content.

Statement 22: A composition according to any one of the preceding Statements 16-19, wherein the metal-doped porous zeolite monolith comprises from about 5 wt % to about 10 wt % metal content.

Statement 23: A composition according to any one of the preceding Statements 16-19, wherein the metal-doped porous zeolite monolith comprises from about 9 wt % to about 12 wt % metal content.

Statement 24: A composition according to any one of the preceding Statements 16-19, wherein the metal-doped porous zeolite monolith comprises from about 2.5 wt % to about 15 wt % metal content.

Statement 25: A composition according to any one of the preceding Statements 16-19, wherein the metal-doped porous zeolite monolith comprises from about 5 wt % to about 15 wt % metal content.

Statement 26: A composition according to any one of the preceding Statements 16-19, wherein the metal-doped porous zeolite monolith is characterized by a metal loading of 1 wt % to about 20 wt %.

Statement 27: A composition according to any one of the preceding Statements 16-19, wherein the metal-doped porous zeolite monolith is characterized by a metal loading of 2.5 wt % to about 12 wt %.

Statement 28: A composition according to any one of the preceding Statements 16-19, wherein the metal-doped porous zeolite monolith is characterized by a metal loading of 5 wt % to about 10 wt %.

Statement 29: A composition according to any one of the preceding Statements 16-19, wherein the metal-doped porous zeolite monolith is characterized by a metal loading of 9 wt % to about 12 wt %.

Statement 30: A composition according to any one of the preceding Statements 16-19, wherein the metal-doped porous zeolite monolith is characterized by a metal loading of 2.5 wt % to about 15 wt %.

Statement 31: A composition according to any one of the preceding Statements 16-19, wherein the metal-doped porous zeolite monolith is characterized by a metal loading of 5 wt % to about 15 wt %.

Statement 32: A composition according to any one of the preceding Statements 16-19, wherein the porous zeolite monolith or the metal-doped porous zeolite monolith has a total pore volume ($V_{total}$) of from about 0.25 cm$^3$/g to about 0.60 cm$^3$/g.

Statement 33: A composition according to any one of the preceding Statements 1-31, wherein the porous zeolite monolith or the metal-doped porous zeolite monolith has a total pore volume ($V_{total}$) of from about 0.2 cm$^3$/g to about 0.70 cm$^3$/g.

Statement 34: A composition according to any one of the preceding Statements 1-31, wherein the porous zeolite monolith or the metal-doped porous zeolite monolith has a total pore volume ($V_{total}$) of from about 0.1 cm$^3$/g to about 0.80 cm$^3$/g.

Statement 35: A composition according to any one of the preceding Statements 1-31, wherein the porous zeolite monolith or the metal-doped porous zeolite monolith has a total pore volume ($V_{total}$) of from about 0.2 cm$^3$/g to about 0.3 cm$^3$/g.

Statement 36: A composition according to any one of the preceding Statements 1-31, wherein the porous zeolite monolith or the metal-doped porous zeolite monolith has a total pore volume ($V_{total}$) of from about 0.15 cm$^3$/g to about 0.35 cm$^3$/g.

Statement 37: A composition according to any one of the preceding Statements 1-31, wherein the porous zeolite monolith or the metal-doped porous zeolite monolith has a total pore volume ($V_{total}$) of from about 0.1 cm$^3$/g to about 0.4 cm$^3$/g.

Statement 38: A composition according to any one of the preceding Statements 1-37, wherein the porous zeolite monolith or the metal-doped porous zeolite monolith has a mesopore volume ($V_{meso}$) of from about 0.15 cm$^3$/g to about 0.35 cm$^3$/g.

Statement 39: A composition according to any one of the preceding Statements 1-37, wherein the porous zeolite monolith or the metal-doped porous zeolite monolith has a mesopore volume ($V_{meso}$) of from about 0.1 cm$^3$/g to about 0.4 cm$^3$/g.

Statement 40: A composition according to any one of the preceding Statements 1-37, wherein the porous zeolite monolith or the metal-doped porous zeolite monolith has a mesopore volume ($V_{meso}$) of from about 0.1 cm$^3$/g to about 0.5 cm$^3$/g.

Statement 41: A composition according to any one of the preceding Statements 1-37, wherein the porous zeolite monolith or the metal-doped porous zeolite monolith has a mesopore volume ($V_{meso}$) of from about 0.1 cm$^3$/g to about 0.2 cm$^3$/g.

Statement 42: A composition according to any one of the preceding Statements 1-37, wherein the porous zeolite monolith or the metal-doped porous zeolite monolith has a mesopore volume ($V_{meso}$) of from about 0.08 cm$^3$/g to about 0.25 cm$^3$/g.

Statement 43: A composition according to any one of the preceding Statements 1-42, wherein the porous zeolite monolith or the metal-doped porous zeolite monolith has a micropore volume ($V_{micro}$) of from about 0.10 cm$^3$/g to about 0.25 cm$^3$/g.

Statement 44: A composition according to any one of the preceding Statements 1-42, wherein the porous zeolite monolith or the metal-doped porous zeolite monolith has a micropore volume ($V_{micro}$) of from about 0.05 cm$^3$/g to about 0.35 cm$^3$/g.

Statement 45: A composition according to any one of the preceding Statements 1-42, wherein the porous zeolite monolith or the metal-doped porous zeolite monolith has a micropore volume ($V_{micro}$) of from about 0.08 cm$^3$/g to about 0.3 cm$^3$/g.

Statement 46: A composition according to any one of the preceding Statements 1-42, wherein the porous zeolite monolith or the metal-doped porous zeolite monolith has a micropore volume ($V_{micro}$) of from about 0.09 cm$^3$/g to about 0.1 cm$^3$/g.

Statement 47: A composition according to any one of the preceding Statements 1-42, wherein the porous zeolite monolith or the metal-doped porous zeolite monolith has a micropore volume ($V_{micro}$) of from about 0.08 cm$^3$/g to about 0.11 cm$^3$/g.

Statement 48: A composition according to any one of the preceding Statements 1-42, wherein the porous zeolite monolith or the metal-doped porous zeolite monolith has a micropore volume ($V_{micro}$) of from about 0.05 cm$^3$/g to about 0.15 cm$^3$/g.

Statement 49: A composition according to any one of the preceding Statements 1-48, wherein the porous zeolite monolith or the metal-doped porous zeolite monolith comprises a plurality of pores, the pores having an average pore diameter from about 15 nanometers to about 75 nanometers.

Statement 50: A composition according to any one of the preceding Statements 1-48, wherein the porous zeolite monolith or the metal-doped porous zeolite monolith comprises a plurality of pores, the pores having an average pore diameter from about 15 nanometers to about 550 nanometers.

Statement 51: A composition according to any one of the preceding Statements 1-48, wherein the porous zeolite monolith or the metal-doped porous zeolite monolith comprises a plurality of pores, the pores having an average pore diameter from about 8 nanometers to about 100 nanometers.

Statement 52: A composition according to any one of the preceding Statements 1-48, wherein the porous zeolite monolith or the metal-doped porous zeolite monolith comprises a plurality of pores, the pores having an average pore diameter from about 10 nanometers to about 40 nanometers.

Statement 53: A composition according to any one of the preceding Statements 1-48, wherein the porous zeolite monolith or the metal-doped porous zeolite monolith comprises a plurality of pores, the pores having an average pore diameter from about 100 nanometers to about 2000 nanometers.

Statement 54: A composition according to any one of the preceding Statements 1-48, wherein the porous zeolite monolith or the metal-doped porous zeolite monolith comprises a plurality of pores, the pores having an average pore diameter from about 10 nanometers to about 2000 nanometers.

Statement 55: A composition according to any one of the preceding Statements 1-54, wherein the porous zeolite monolith or the metal-doped porous zeolite monolith comprises a weak acid amount of from about 0.13 mmol/g to about 0.37 mmol/g and a strong acid amount of from about 0.3 mmol/g to about 0.65 mmol/g as measured by ammonia temperature programmed desorption.

Statement 56: A composition according to any one of the preceding Statements 1-54, wherein the porous zeolite monolith or the metal-doped porous zeolite monolith comprises a weak acid amount of from about 0.1 mmol/g to about 0.4 mmol/g and a strong acid amount of from about 0.2 mmol/g to about 0.8 mmol/g as measured by ammonia temperature programmed desorption.

Statement 57: A composition according to any one of the preceding Statements 1-54, wherein the porous zeolite monolith or the metal-doped porous zeolite monolith comprises a weak acid amount of from about 0.3 mmol/g to about 0.56 mmol/g and a strong acid amount of from about 0.07 mmol/g to about 0.16 mmol/g as measured by ammonia temperature programmed desorption.

Statement 58: A composition according to any one of the preceding Statements 1-54, wherein the porous zeolite monolith or the metal-doped porous zeolite monolith comprises a weak acid amount of from about 0.25 mmol/g to about 0.6 mmol/g and a strong acid amount of from about 0.05 mmol/g to about 0.2 mmol/g as measured by ammonia temperature programmed desorption.

Statement 59: A composition according to any one of the preceding Statements 1-58, wherein the composition is a catalyst for the catalytic cracking of alkanes to produce light olefins.

Statement 60: A composition according to any one of the preceding Statements 1-58, wherein the composition is a catalyst for the catalytic conversion of alkanes to light olefins.

Statement 61: A composition according to any one of the preceding Statements 1-58, wherein the composition is a catalyst for the catalytic conversion of alkanes to light olefins and benzene, toluene, and xylene (BTX).

Statement 62: A composition according to any one of the preceding Statements 59-61, wherein the light olefins is selected from the group consisting of ethylene, propylene, butylene, and any combination thereof.

Statement 63: A composition according to any one of the preceding Statements 1-62, wherein the alkanes is selected from the group consisting of light alkanes.

Statement 64: A composition according to any one of the preceding Statements 1-62, wherein the alkanes is selected from the group consisting of $C_3$-$C_{15}$ alkanes.

Statement 65: A composition according to any one of the preceding Statements 1-62, wherein the alkanes is n-hexane.

Statement 66: A porous zeolite monolith composition for the catalytic cracking of alkanes, the composition comprising: a HZSM-5 zeolite monolith comprising a MFI framework; and a coating on at least a portion of the HZSM-5 zeolite monolith, the coating comprising a silicoaluminophosphate with chabazite (SAPO-34) framework; wherein the composition is prepared layer by layer using a 3D printer such that the composition comprises a plurality of micropores and a plurality of mesopores, the micropores having a diameter of greater than 15 nanometers and the mesopores having a diameter of from 2 nanometers to 15 nanometers.

Statement 67: A composition according to Statement 66, wherein the composition is characterized by a selectivity to light olefins of at least about 50.0% at a temperature of 650° C.

Statement 68: A composition according to Statement 66, wherein the composition is characterized by a selectivity to light olefins of at least about 53.0% at a temperature of 650° C.

Statement 69: A composition according to any one of the preceding Statements 66-68, wherein the composition comprises a total pore volume ($V_{total}$) of from about 0.25 cm$^3$/g to about 0.60 cm$^3$/g.

Statement 70: A composition according to any one of the preceding Statements 66-68, wherein the composition comprises a total pore volume ($V_{total}$) of from about 0.2 cm$^3$/g to about 0.35 cm$^3$/g.

Statement 71: A composition according to any one of the preceding Statements 66-70, wherein the composition comprises a mesopore volume ($V_{meso}$) of from about 0.15 cm$^3$/g to about 0.30 cm$^3$/g.

Statement 72: A composition according to any one of the preceding Statements 66-70, wherein the composition comprises a mesopore volume ($V_{meso}$) of from about 0.15 cm$^3$/g to about 0.25 cm$^3$/g.

Statement 73: A composition according to any one of the preceding Statements 66-72, wherein the composition comprises a micropore volume ($V_{micro}$) of from about 0.10 cm$^3$/g to about 0.15 cm$^3$/g.

Statement 74: A composition according to any one of the preceding Statements 66-72, wherein the composition comprises a micropore volume ($V_{micro}$) of from about 0.08 cm$^3$/g to about 0.13 cm$^3$/g.

Statement 75: A composition according to any one of the preceding Statements 66-74, wherein the composition comprises a plurality of pores, the pores having an average pore diameter from about 15 nanometers to about 75 nanometers.

Statement 76: A composition according to any one of the preceding Statements 66-74, wherein the composition comprises a plurality of pores, the pores having an average pore diameter from about 15 nanometers to about 550 nanometers.

Statement 77: A composition according to any one of the preceding Statements 66-76, wherein the composition comprises a weak acid amount of from about 0.25 mmol/g to about 0.37 mmol/g and a strong acid amount of from about 0.2 mmol/g to about 0.32 mmol/g as measured by ammonia temperature programmed desorption.

Statement 78: A porous zeolite monolith composition for the catalytic cracking of alkanes, the composition comprising: a HY zeolite monolith comprising a FAU framework; and a coating on at least a portion of the HY zeolite monolith, the coating comprising a silicoaluminophosphate with chabazite (SAPO-34) framework; wherein the composition is prepared layer by layer using a 3D printer such that the composition comprises a plurality of micropores and a plurality of mesopores, the micropores having a diameter of greater than 15 nanometers and the mesopores having a diameter of from 2 nanometers to 15 nanometers.

Statement 79: A composition according to Statement 78, wherein the composition is characterized by a selectivity to light olefins of at least about 55.0% at a temperature of 600° C.

Statement 80: A composition according to Statement 78, wherein the composition is characterized by a selectivity to light olefins of at least about 57.0% at a temperature of 600° C.

Statement 81: A composition according to Statement 78, wherein the composition is characterized by a selectivity to benzene, toluene, and xylene (BTX) of at least about 27.5% at a temperature of 600° C.

Statement 82: A composition according to any one of the preceding Statements 78-81, wherein the composition comprises a total pore volume ($V_{total}$) of from about 0.25 cm$^3$/g to about 0.60 cm$^3$/g.

Statement 83: A composition according to any one of the preceding Statements 78-81, wherein the composition comprises a total pore volume ($V_{total}$) of from about 0.25 cm$^3$/g to about 0.35 cm$^3$/g.

Statement 84: A composition according to any one of the preceding Statements 78-83, wherein the composition comprises a mesopore volume ($V_{meso}$) of from about 0.15 cm$^3$/g to about 0.30 cm$^3$/g.

Statement 85: A composition according to any one of the preceding Statements 78-83, wherein the composition comprises a mesopore volume ($V_{meso}$) of from about 0.15 cm$^3$/g to about 0.25 cm$^3$/g.

Statement 86: A composition according to any one of the preceding Statements 78-85, wherein the composition comprises a micropore volume ($V_{micro}$) of from about 0.10 cm$^3$/g to about 0.25 cm$^3$/g.

Statement 87: A composition according to any one of the preceding Statements 78-85, wherein the composition comprises a micropore volume ($V_{micro}$) of from about 0.08 cm$^3$/g to about 0.13 cm$^3$/g.

Statement 88: A composition according to any one of the preceding Statements 78-87, wherein the composition comprises a plurality of pores, the pores having an average pore diameter from about 15 nanometers to about 75 nanometers.

Statement 89: A composition according to any one of the preceding Statements 78-87, wherein the composition comprises a plurality of pores, the pores having an average pore diameter from about 15 nanometers to about 550 nanometers.

Statement 90: A composition according to any one of the preceding Statements 78-89, wherein the composition comprises a weak acid amount of from about 0.1 mmol/g to about 0.25 mmol/g and a strong acid amount of from about 0.15 mmol/g to about 0.30 mmol/g as measured by ammonia temperature programmed desorption.

Statement 91: A metal-doped porous zeolite monolith composition for the catalytic cracking of alkanes, the composition comprising: a ZSM-5 zeolite monolith comprising a MFI framework, the ZSM-5 zeolite monolith comprising a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof; wherein the composition is prepared layer by layer using a 3D printer such that the composition comprises a plurality of micropores and a plurality of mesopores, the micropores having a diameter of greater than 15 nanometers and the mesopores having a diameter of from 2 nanometers to 15 nanometers.

Statement 92: A composition according to Statement 91, wherein the composition comprises from about 1 wt % to about 20 wt % metal content.

Statement 93: A composition according to Statement 91, wherein the composition comprises from about 2.5 wt % to about 12 wt % metal content.

Statement 94: A composition according to Statement 91, wherein the composition comprises from about 5 wt % to about 10 wt % metal content.

Statement 95: A composition according to Statement 91, wherein the composition comprises from about 9 wt % to about 12 wt % metal content.

Statement 96: A composition according to Statement 91, wherein the composition comprises from about 2.5 wt % to about 15 wt % metal content.

Statement 97: A composition according to Statement 91, wherein the composition comprises from about 5 wt % to about 15 wt % metal content.

Statement 98: A composition according to any one of the preceding Statements 91-97, wherein the composition comprises a total pore volume ($V_{total}$) of from about 0.2 cm$^3$/g to about 0.3 cm$^3$/g.

Statement 99: A composition according to any one of the preceding Statements 91-98, wherein the composition comprises a mesopore volume ($V_{meso}$) of from about 0.1 cm$^3$/g to about 0.2 cm$^3$/g.

Statement 100: A composition according to any one of the preceding Statements 91-99, wherein the composition comprises a micropore volume ($V_{micro}$) of from about 0.08 cm$^3$/g to about 0.10 cm$^3$/g.

Statement 101: A composition according to any one of the preceding Statements 91-100, wherein the composition comprises a plurality of pores, the pores having an average pore diameter from about 8 nanometers to about 75 nanometers.

Statement 102: A composition according to any one of the preceding Statements 91-100, wherein the composition comprises a plurality of pores, the pores having an average pore diameter from about 8 nanometers to about 2000 nanometers.

Statement 103: A composition according to any one of the preceding Statements 91-102, wherein the composition comprises a weak acid amount of from about 0.3 mmol/g to about 0.6 mmol/g and a strong acid amount of from about 0.05 mmol/g to about 0.20 mmol/g as measured by ammonia temperature programmed desorption.

Statement 104: A method for preparing a porous zeolite monolith catalyst for the catalytic cracking of alkanes, the method comprising: generating, using a 3D printer, a porous zeolite monolith catalyst from a zeolite paste by layer by layer deposition.

Statement 105: A method according to Statement 104, wherein the zeolite paste comprises a zeolite powder, a binder, a plasticizer, and water.

Statement 106: A method according to Statement 105, wherein the binder comprises bentonite clay.

Statement 107: A method according to Statement 105 or Statement 106, wherein the plasticizer comprises methyl cellulose.

Statement 108: A method according to any one of the preceding Statements 105-107, wherein the zeolite powder is selected from the group consisting of the hydrogen form of ZSM-5 zeolite (HZSM-5) and the hydrogen form of Y zeolite (HY, CBV780, SiO2/Al2O3=80).

Statement 109: A method according to any one of the preceding Statements 104-108, wherein the zeolite paste comprises a metal oxide precursor.

Statement 110: A method according to Statement 109, wherein the metal oxide precursor is a transition metal oxide precursor.

Statement 111: A method according to Statement 109, wherein the metal oxide precursor is selected from the group consisting of $Cr(NO_3)_3.9H_2O$, $Cu(NO_3)_2.2.5H_2O$, $Ni(NO_3)_2.6H_2O$, and $Y(NO_3)_3.6H_2O$.

Statement 112: A method according to any one of the preceding Statements 104-108, wherein the zeolite paste comprises a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof.

Statement 113: A method according to any one of the preceding Statements 104-108, wherein the zeolite paste comprises an aqueous nitrate solution comprising a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof.

Statement 114: A method according to any one of the preceding Statements 104-108, wherein the zeolite paste comprises 87.5 wt % zeolite powder, 10 wt % binder, and 2.5 wt % plasticizer.

Statement 115: A method according to any one of the preceding Statements 104-114, wherein the zeolite monolith is generated such that the zeolite monolith comprises a honeycomb-like structure.

Statement 116: A method according to any one of the preceding Statements 104-114, wherein the zeolite monolith is generated such that the zeolite monolith comprises a plurality of interconnected channels.

Statement 117: A method according to any one of the preceding Statements 104-114, wherein the zeolite monolith is generated such that the zeolite monolith comprises a plurality of micropores and a plurality of mesopores, the micropores having a diameter of greater than 15 nanometers and the mesopores having a diameter of from 2 nanometers to 15 nanometers.

Statement 118: A method according to any one of the preceding Statements 104-117, further comprising forming a coating on the porous zeolite monolith catalyst, the coating comprising a silicoaluminophosphate with chabazite (SAPO-34) framework.

Statement 119: A method according to Statement 118, wherein the coating is formed by a secondary growth method.

Statement 120: A method according to Statement 118, wherein the secondary growth method comprises: preparing a plurality of SAPO-34 seeds; contacting the generated porous zeolite monolith catalyst with the SAPO-34 seeds to form a seeded porous zeolite monolith catalyst; and contacting the seeded porous zeolite monolith catalyst with a SAPO-34 synthesis solution to form a SAPO-34 coating on the porous zeolite monolith catalyst.

Statement 121: A method according to Statement 120, wherein the SAPO-34 seeds are prepared by mixing aluminum isopropoxide, colloidal silica, tetraethylammonium hydroxide, and phosphoric acid.

Statement 122: A method according to Statement 120 or Statement 121, wherein the SAPO-34 synthesis solution comprises a mixture of aluminum isopropoxide, colloidal silica, tetraethylammonium hydroxide, and phosphoric acid.

Statement 123: A method for the catalytic cracking of alkanes, the method comprising: contacting an alkane with a catalyst according to the composition of any one of the preceding Statements 1-103.

Statement 124: A method according to Statement 123, wherein the contacting an alkane with a catalyst occurs at a temperature of from about 600° C. to about 650° C.

Statement 125: A method according to Statement 123, wherein the contacting an alkane with a catalyst occurs at a temperature of from about 200° C. to about 850° C.

Statement 126: A method according to Statement 123, wherein the contacting an alkane with a catalyst occurs at a temperature of from about 400° C. to about 800° C.

Statement 127: A method according to any one of the preceding Statements 123-126, further comprising regenerating the catalyst a plurality of times by heating the catalyst to a temperature of up to 760° C.

Statement 128: A method according to any one of the preceding Statements 123-127, wherein the catalyst is characterized by a 98% or greater conversion of n-hexane at 650° C. after two regeneration cycles.

Statement 129: A method according to any one of the preceding Statements 123-128, wherein the catalyst exhibits a selectivity to light olefins of at least 50.0% at a temperature of 650° C.

Statement 130: A method according to any one of the preceding Statements 123-128, wherein the catalyst exhibits a selectivity to light olefins of at least 53.0% at a temperature of 650° C.

Statement 131: A method according to any one of the preceding Statements 123-128, wherein the catalyst exhibits a selectivity to light olefins of at least 55.0% at a temperature of 600° C.

Statement 132: A method according to any one of the preceding Statements 123-128, wherein the catalyst exhibits a selectivity to light olefins of at least 57.0% at a temperature of 600° C.

Statement 133: A method according to any one of the preceding Statements 123-128, wherein the catalyst exhibits a selectivity to benzene, toluene, and xylene (BTX) of at least 27.5% at a temperature of 600° C.

Statement 134: A method according to any one of the preceding Statements 123-133, wherein the alkanes is selected from the group consisting of light alkanes.

Statement 135: A method according to any one of the preceding Statements 123-133, wherein the alkanes is selected from the group consisting of $C_3$-$C_{15}$ alkanes.

Statement 136: A method according to any one of the preceding Statements 123-133, wherein the alkanes is n-hexane.

What is claimed is:

1. A porous zeolite monolith composition for the catalytic cracking of alkanes, the composition comprising:
    a HZSM-5 zeolite monolith comprising a MFI framework; and
    a coating on at least a portion of the HZSM-5 zeolite monolith, the coating comprising a silicoaluminophosphate with chabazite framework;
    wherein the composition is prepared layer by layer using a 3D printer such that the composition comprises a plurality of micropores and a plurality of mesopores, the micropores having a diameter of less than 2 nanometers and the mesopores having a diameter of from 2 nanometers to 50 nanometers.

2. The composition according to claim 1, wherein the composition is characterized by a selectivity to light olefins of at least about 50.0% at a temperature of 650° C.

3. The composition according to claim 1, wherein the composition comprises a total pore volume ($V_{total}$) of from about 0.25 cm$^3$/g to about 0.60 cm$^3$/g, a mesopore volume ($V_{meso}$) of from about 0.15 cm$^3$/g to about 0.30 cm$^3$/g, and a micropore volume ($V_{micro}$) of f from about 0.10 cm$^3$/g to about 0.15 cm$^3$/g.

4. The composition according to claim 1, wherein the composition comprises a plurality of pores, the pores having an average pore diameter from about 15 nanometers to about 75 nanometers.

5. The composition according to claim 1, wherein the composition comprises a weak acid amount of from about 0.25 mmol/g to about 0.37 mmol/g and a strong acid amount of from about 0.2 mmol/g to about 0.32 mmol/g as measured by ammonia temperature programmed desorption.

6. A porous zeolite monolith composition for the catalytic cracking of alkanes, the composition comprising:
    a HY zeolite monolith comprising a FAU framework; and
    a coating on at least a portion of the HY zeolite monolith, the coating comprising a silicoaluminophosphate with chabazite framework;
    wherein the composition is prepared layer by layer using a 3D printer such that the composition comprises a plurality of micropores and a plurality of mesopores, the micropores having a diameter of less than 2 nanometers and the mesopores having a diameter of from 2 nanometers to 50 nanometers.

7. The composition according to claim 6, wherein the composition is characterized by a selectivity to light olefins of at least about 55.0% at a temperature of 600° C.

8. The composition according to claim 6, wherein the composition is characterized by a selectivity to light olefins of at least about 57.0% at a temperature of 600° C.

9. The composition according to claim 6, wherein the composition is characterized by a selectivity to benzene, toluene, and xylene (BTX) of at least about 27.5% at a temperature of 600° C.

10. The composition according to claim 6, wherein the composition comprises a total pore volume ($V_{total}$) of from about 0.25 cm$^3$/g to about 0.60 cm$^3$/g, a mesopore volume ($V_{meso}$) of from about 0.15 cm$^3$/g to about 0.30 cm$^3$/g, and a micropore volume ($V_{micro}$) of from about 0.10 cm$^3$/g to about 0.25 cm$^3$/g.

11. The composition according to claim 6, wherein the composition comprises a plurality of pores, the pores having an average pore diameter from about 15 nanometers to about 75 nanometers.

12. The composition according to claim 6, wherein the composition comprises a weak acid amount of from about 0.1 mmol/g to about 0.25 mmol/g and a strong acid amount of from about 0.15 mmol/g to about 0.30 mmol/g as measured by ammonia temperature programmed desorption.

13. A metal-doped porous zeolite monolith composition for the catalytic cracking of alkanes, the composition comprising:
    a ZSM-5 zeolite monolith comprising a MFI framework, the ZSM-5 zeolite monolith comprising a metal selected from the group consisting of chromium (Cr), copper (Cu), nickel (Ni), yttrium (Y), cesium (Cs), gallium (Ga), lanthanum (La), magnesium (Mg), strontium (Sr), zinc (Zn), iron (Fe), cerium (Ce), vanadium (V), and any combination thereof;
    wherein the composition is prepared layer by layer using a 3D printer such that the composition comprises a plurality of micropores and a plurality of mesopores, the micropores having a diameter of less than 2 nanometers and the mesopores having a diameter of from 2 nanometers to 50 nanometers.

14. The composition according to claim 13, wherein the composition comprises from about 1 wt % to about 20 wt % metal content.

15. The composition according to claim 13, wherein the composition comprises a total pore volume ($V_{total}$) of from about 0.2 cm$^3$/g to about 0.3 cm$^3$/g, a mesopore volume ($V_{meso}$) of from about 0.1 cm$^3$/g to about 0.2 cm$^3$/g, and a micropore volume ($V_{micro}$) of from about 0.08 cm$^3$/g to about 0.10 cm$^3$/g.

16. The composition according to claim 13, wherein the composition comprises a plurality of pores, the pores having an average pore diameter from about 8 nanometers to about 75 nanometers.

17. The composition according to claim 13, wherein the composition comprises a weak acid amount of from about 0.3 mmol/g to about 0.6 mmol/g and a strong acid amount of from about 0.05 mmol/g to about 0.20 mmol/g as measured by ammonia temperature programmed desorption.

18. A method for the catalytic cracking of alkanes, the method comprising:
    contacting an alkane with a catalyst composition according to claim 13.

* * * * *